United States Patent
Shin et al.

(10) Patent No.: US 9,956,256 B2
(45) Date of Patent: May 1, 2018

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Bo Kyung Son, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days. days.

(21) Appl. No.: 15/304,429

(22) PCT Filed: Apr. 14, 2015

(86) PCT No.: PCT/KR2015/003706
§ 371 (c)(1),
(2) Date: Oct. 14, 2016

(87) PCT Pub. No.: WO2015/160166
PCT Pub. Date: Oct. 22, 2015

(65) Prior Publication Data
US 2017/0189460 A1    Jul. 6, 2017

(30) Foreign Application Priority Data
Apr. 15, 2014  (KR) .................. 10-2014-0044995

(51) Int. Cl.
*C12N 7/00*     (2006.01)
*A61K 35/76*   (2015.01)

(52) U.S. Cl.
CPC ............... *A61K 35/76* (2013.01); *C12N 7/00* (2013.01)

(58) Field of Classification Search
None
See application file for complete search history.

(56) References Cited

U.S. PATENT DOCUMENTS

2012/0156174 A1    6/2012    Yang et al.

FOREIGN PATENT DOCUMENTS

| KR | 10-2009-0030385 A | 3/2009 |
| KR | 10-2009-0030386 A | 3/2009 |
| KR | 10-2012-0013149 A | 2/2012 |
| KR | 10-2012-0070533 A | 6/2012 |
| KR | 10-2013-0021677 A | 3/2013 |
| KR | 10-2013-0031004 A | 3/2013 |
| WO | 2013/042964 A2 | 3/2013 |
| WO | 2013-169102 A1 | 11/2013 |

OTHER PUBLICATIONS

BLAST search results for 1-3000 nt of SEQ ID No. 1; searched Sep. 30, 2017 (Year: 2017).*

(Continued)

*Primary Examiner* — Michelle S Horning
(74) *Attorney, Agent, or Firm* — Knobbe Martens Olson & Bear LLP

(57) ABSTRACT

The present invention relates to a novel bacteriophage ΦCJ26 (KCCM11464P) and a composition comprising the same as an active ingredient. In addition, the present invention relates to a method for preventing and/or treating infectious diseases caused by *Salmonella* by using the bacteriophage ΦCJ26 (KCCM11464P) or the composition.

11 Claims, 3 Drawing Sheets

(56) References Cited

OTHER PUBLICATIONS

BLAST search results for 1-3000 nt of SEQ ID No. 2; searched Sep. 30, 2017 (Year: 2017).*

BLAST search results for 1-3000 nt of SEQ ID No. 3; searched Sep. 30, 2017 (Year: 2017).*

International Search Report dated Jun. 29, 2015 of PCT/KR2015/003706 which is the parent application and its English translation—4 pages.

Notice of Allowance dated Jan. 27, 2016 of corresponding Korean Patent Application No. 10-2014-0044995—1 page.

Office Action dated Aug. 23, 2017 of corresponding Japanese Patent Application No. 2016-562871—3 pages.

Extended European Search Report dated Sep. 25, 2017 of corresponding European Patent Application No. 15780619.1—10 pages.

Switt et al., "*Salmonella bacteriophage* diversity reflects host diversity on dairy farms", Food Microbiology, vol. 36, 2013, pp. 275-285.

Marti et al., "Long tail fibres of the novel broad-host-range T-even bacteriophage S16 specifically recognize *Salmonella ompC*", Molecular Microbiology, vol. 87, No. 4, 2013, pp. 818-834.

Ricci et al., "Exploiting the Role of ToIC in Pathogenicity: Identification of a Bacteriophage for Eradication of *Salmonella serovars* from Poultry", Applied and Environmental Microbiology, vol. 76, No. 5, Mar. 2010, pp. 1704-1706.

Heringa et al., "Use of a Mixture of Bacteriophages for Biological Control of *Salmonella enterica* Strains in Compost", Applied and Environmental Microbiology, vol. 76, No. 15, Aug. 2010, pp. 5327-5332.

Goncalves et al., "Bacteriophage-induced reduction in *Salmonella enteritidis* counts in the crop of broiler chickens undergoing preslaughter feed withdrawal", Poultry Science, 2014, vol. 93, pp. 216-220.

* cited by examiner

[Fig. 1]
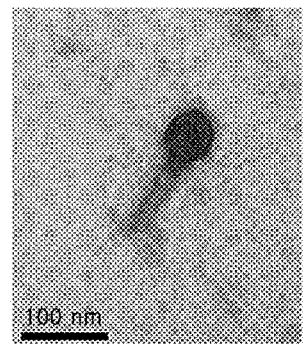
[Fig. 2]
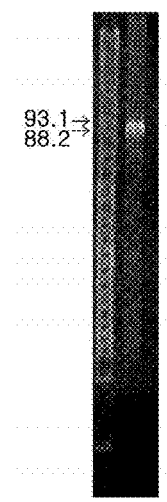
[Fig. 3]
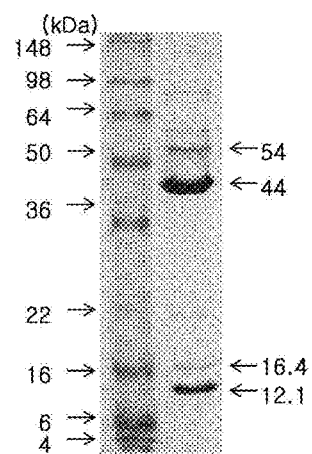

[Fig. 4]
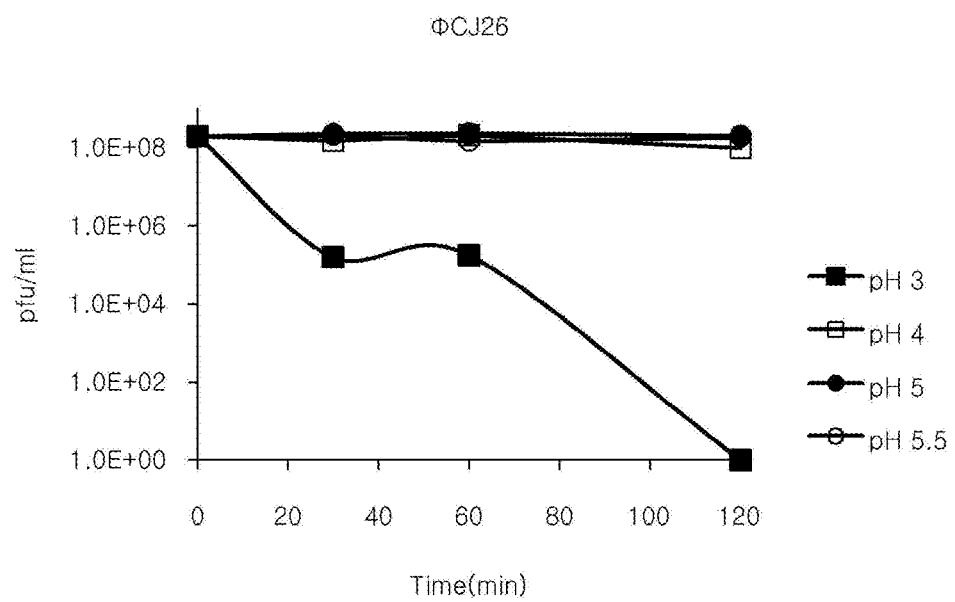
[Fig. 5]
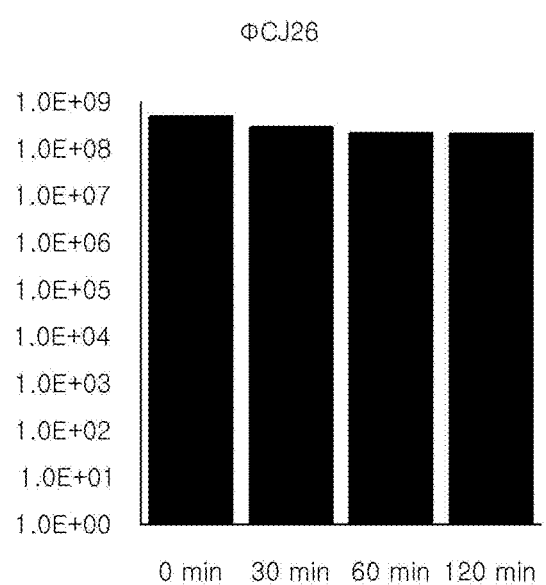

[Fig. 6]
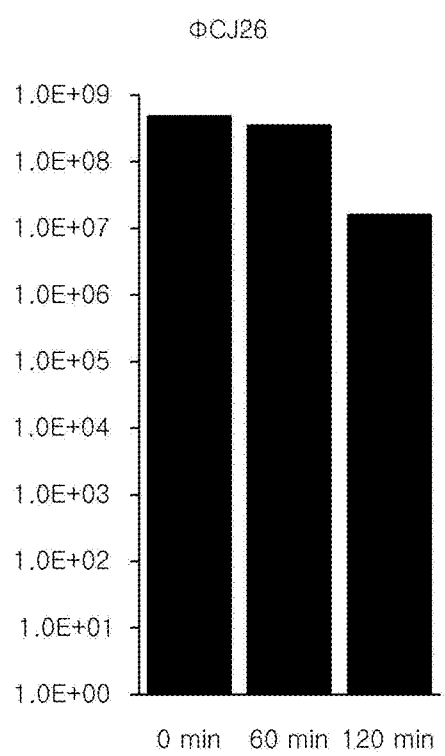

BACTERIOPHAGE AND COMPOSITION COMPRISING SAME

REFERENCE TO SEQUENCE LISTING

This application incorporates by reference the sequence listing submitted as ASCII text filed via EFS-Web Oct. 31, 2016, and updated by a file entitled "24881566_1.txt" created and last modified on Dec. 21, 2016, which is 113,502 bytes in size. The information in the electronic format of the Sequence Listing is incorporated herein by reference in its entirety.

TECHNICAL FIELD

The present invention relates to a novel bacteriophage having a specific ability to kill *Salmonella*, a composition including the same, and a method for preventing or treating infectious diseases caused by *Salmonella* using the novel bacteriophage or the composition.

BACKGROUND ART

*Salmonella* is a genus of anaerobic, Gram-negative bacteria (facultative anaerobes) of family Enterobacteriaceae, and is a non-endospore-forming *bacillus* having peritrichous flagella for mobility. *Salmonella* is a pathogenic microorganism that causes various diseases not only in various livestock but also in humans.

Salmonellosis in humans is mainly caused by ingestion of animal products such as pork and the like. Reports say that several strains of *Salmonella* have specificity for poultry and thus cause infection in poultry, causing enormous economic damage to poultry farms and consumers, and it is known that *Salmonella* infected poultry and ingestion of such infected poultry cause food poisoning in humans.

Specifically, according to 2005's statistics of the US Centers for Disease Control and Prevention (CDC), nine strains of *Salmonella*, among *Salmonella* strains isolated from humans suffering from food poisoning caused by *Salmonella*, match *Salmonella* strains derived from poultry, and it was confirmed that the most predominant *Salmonella* strain isolated from humans suffering from food poisoning coincides with the most predominant *Salmonella* strain isolated from chickens.

Bacteriophage refers to a bacteria-specific virus that infects a specific bacterium and prevents and inhibits growth of the bacterium. As bacteriophages have stronger host specificity than antibiotics and recent emergence of bacteria resistant to antibiotics and residual antibiotics in animals become serious, application of bacteriophages has attracted great attention.

However, most studies on bacteriophages are focused on controlling *Escherichia coli*, *Listeria*, and *Chlorstridium*. *Salmonella* is also contagious both in humans and animals, has continued to cause infectious diseases, and is capable of growing in a phagocyte which intakes bacteria, thereby being resistant to antibiotics. Therefore, there is a need for bacteriophages which can effectively control *Salmonella*, and particularly, there is a need for bacteriophages and development of relevant technologies in order to control *Salmonella* in poultry to prevent infectious diseases caused by *Salmonella* in poultry and in order to prevent poultry-mediated food poisoning in humans.

DISCLOSURE

Technical Problem

As a result of earnest investigation aimed at effectively preventing and treating infectious diseases caused by *Salmonella*, the present inventors provide a novel bacteriophage ΦCJ26 (KCCM11464P) having a specific ability to kill *Salmonella*.

In addition, in order to solve the emergence of resistant bacteria due to use of antibiotics and residual problems of antibiotics in meat, the present invention provides antibiotics, additives for feeds, additives for drinking water, feeds, drinking water, disinfectants or detergents, including the bacteriophage ΦCJ26 (KCCM11464P) as an active ingredient.

Further, the present invention provides a composition for preventing and/or treating not only infectious diseases caused by *Salmonella* in poultry but also food poisoning in humans, including the bacteriophage ΦCJ26 (KCCM11464P) as an active ingredient, and a method for preventing or treating diseases using the same.

Technical Solution

One aspect of the present invention provides a novel bacteriophage ΦCJ26 (KCCM11464P) having a specific ability to kill *Salmonella*.

Another aspect of the present invention provides a composition for preventing or treating infectious diseases caused by *Salmonella*, including a bacteriophage ΦCJ26 (KCCM11464P) as an active ingredient.

A further aspect of the present invention provides antibiotics, additives for feeds, additives for drinking water, feeds, drinking water, disinfectants or detergents, including a bacteriophage ΦCJ26 (KCCM11464P) as an active ingredient.

Yet another aspect of the present invention provides a method for preventing or treating infectious diseases caused by *Salmonella*, including: administering a bacteriophage ΦCJ26 (KCCM11464P) or a composition including the bacteriophage ΦCJ26 (KCCM11464P) as an active ingredient to a non-human animal.

Advantageous Effects

The bacteriophage ΦCJ26 (KCCM11464P) according to the present invention has a specific ability to kill *Salmonella*.

In addition, the bacteriophage ΦCJ26 (KCCM11464P) according to the present invention has excellent acid resistance, heat resistance, and drying resistance, and thus can be used not only as an agent for preventing or treating infectious diseases caused by *Salmonella* at various ranges of temperature, pH, and drying conditions, but also as antibiotics, additives for feeds, additives for drinking water, feeds, drinking water, disinfectants, detergents, and the like, including the bacteriophage ΦCJ26 (KCCM11464P) as an active ingredient.

Further, the present invention provides the bacteriophage ΦCJ26 (KCCM11464P) or antibiotics including the same as an active ingredient, which have specificity for *Salmonella* as compared with typical antibiotics so as to selectively kill specific pathogenic bacteria without killing beneficial bacteria and do not induce drug resistance, resulting in extension of lifetime of products as compared with typical antibiotics.

Further, the present invention can prevent or treat infectious diseases caused by *Salmonella* by administering the bacteriophage ΦCJ26 (KCCM11464P) or the composition including the bacteriophage ΦCJ26 (KCCM11464P) as an active ingredient to poultry.

DESCRIPTION OF DRAWINGS

FIG. 1 is an electron microscope image of a novel bacteriophage ΦCJ26 (KCCM11464P) (hereinafter referred to as 'ΦCJ26').

FIG. 2 shows results of pulsed field gel electrophoresis (PFGE) of a novel bacteriophage ΦCJ26.

FIG. 3 shows results of sodium dodecyl sulfate polyacrylamide gel electrophoresis (SDS-PAGE) of a novel bacteriophage ΦCJ26.

FIG. 4 is a graph depicting results of acid resistance experiment of a novel bacteriophage ΦCJ26.

FIG. 5 is a graph depicting results of heat resistance experiment of a novel bacteriophage ΦCJ26.

FIG. 6 is a graph depicting results of drying resistance experiment of a novel bacteriophage @CJ26.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ26 (KCCM11464P) (hereinafter referred to as 'ΦCJ26') having a specific ability to kill *Salmonella* subspecies (ssp.).

*Salmonella* is a pathogenic microorganism that infects various livestock and causes various diseases, and specifically, can cause food poisoning in humans when chicken infected with *Salmonella* is ingested, and thus is known as the most frequent causative bacterium for food poisoning among pathogens causing food-mediated (foodborne) diseases in Korea.

Currently, reports say that *Salmonella* includes over 2500 serotypes which are broadly divided into strains having host specificity depending on animals and strains having no host specificity, and are found as parasitic bacteria in various animals.

Examples of *Salmonella* according to serological classification may include *Salmonella senftenberg*, *Salmonella derby*, *Salmonella typhimurium*, *Salmonella paratyphi* A or C, *Salmonella schottmulleri*, *Salmonella choleraesuis*, *Salmonella montevideo*, *Salmonella newport*, *Salmonella enteritidis*, *Salmonella gallinarum*, *Salmonella pullorum*, *Salmonella mbandaka*, *Salmonella abortusovi*, *Salmonella abortusequi*, *Salmonella dublin*, *Salmonella sofia*, *Salmonella Thomson*, *Salmonella havana*, *Salmonella bovismorbificans*, *Salmonella kentucky*, *Salmonella infantis*, *Salmonella hadar*, *Salmonella arizonae* and *Salmonella anatum*, without being limited thereto.

Specifically, *Salmonella* according to one embodiment of the present invention may be strains of *Salmonella* derived from poultry, and examples of strains of *Salmonella* may be at least one selected from the group consisting of *Salmonella senftenberg*, *Salmonella montevideo*, *Salmonella newport*, *Salmonella Kentucky*, *Salmonella mbandaka*, *Salmonella infantis*, *Salmonella hader*, *Salmonella derby*, *Salmonella thomson* and *Salmonella choleraesuis*, without being limited thereto.

Herein, poultry is a generic name for domestic fowl. Poultry is not particularly limited, and may be at least one selected from the group consisting of chickens, geese, turkeys, and the like. Specifically, *Salmonella* according to this embodiment may be derived from chickens.

According to this embodiment, *Salmonella* grows well on common media and is capable of growing at a temperature of about 7° C. to about 48° C. with ideal growth temperature ranging from about 35° C. to about 37° C. Specifically, expression of pathogenic factors is effectively performed at about 42° C. Further, *Salmonella* can grow at a pH ranging from 4.5 to 9.0.

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ26 according to the embodiment of the present invention is a bacteriophage that has species specificity of selectively infecting *Salmonella* and morphologically belongs to family Siphoviridae having an icosahedral capsid and a long non-contractile tail (see FIG. 1). Homology between a nucleotide sequence of the bacteriophage ΦCJ26 and decoded nucleotide sequences of other bacteriophages is compared and results are shown in Table 1. The bacteriophage ΦCJ26 shows stable acid resistance at pH 4.0 to pH 5.5 without losing activity (FIG. 4), and in terms of heat resistance, the bacteriophage ΦCJ26 shows no activity decline when exposed to 60° C. for 2 hours (FIG. 5). In terms of drying resistance, the bacteriophage ΦCJ26 shows activity decline of about 1 log after drying (FIG. 6). Partial DNA nucleotide sequences of the bacteriophage ΦCJ26 are set forth in SEQ ID NOs: 1 to 3 of Sequence List.

The bacteriophage ΦCJ26 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11464P.

Another embodiment of the present invention provides a composition for preventing or treating infectious diseases caused by *Salmonella*, including the bacteriophage ΦCJ26 as an active ingredient.

Since the bacteriophage ΦCJ26 exhibits antibacterial activity capable of specifically killing *Salmonella*, the bacteriophage ΦCJ26 can be utilized in prevention or treatment of diseases caused by infection with *Salmonella*. Examples of infectious diseases caused by *Salmonella* include salmonellosis, without being limited thereto.

Herein, the term "salmonellosis" refers to an acute or chronic, digestive epidemic disease due to infection with *Salmonella*, and symptoms thereof include fever, gastroenteritis, or sepsis as a main symptom with accompanying pneumonia, encephalitis, arthritis, miscarriage, fever, diarrhea, cyanoderma, and the like. Some subspecies can cause infectious diseases in both humans and animals, such as food poisoning due to ingestion of meat of livestock infected with *Salmonella*.

Herein, the term "preventing" or "prevention" refers to all actions to inhibit the diseases or delay occurrence of the diseases by administering the bacteriophage ΦCJ26 and/or the composition including the bacteriophage ΦCJ26 as an active ingredient to a subject.

Herein, the term "treating"" or "treatment" refers to all actions to improve or ameliorate symptoms of infectious diseases by administering the bacteriophage ΦCJ26 and/or the composition including the bacteriophage ΦCJ26 as an active ingredient to a subject.

The composition for preventing or treating infectious diseases caused by *Salmonella* according to this embodiment may include the bacteriophage ΦCJ26 in amounts of $5 \times 10^2$ pfu/ml to $5 \times 10^{12}$ pfu/ml, specifically, $1 \times 10^6$ pfu/ml to $1 \times 10^{10}$ pfu/ml.

The composition for preventing or treating infectious diseases caused by *Salmonella* according to this embodiment may further include pharmaceutically acceptable carriers, and may be formulated with the carriers to provide foods, medicines, additives for feeds or additives for drinking water, and the like.

Herein, the term "pharmaceutically acceptable carriers" refers to carriers or diluents that do not stimulate an organism and do not inhibit biological activity and properties of administered compounds.

Types of carriers applicable to this embodiment are not particularly limited and any carriers commonly used in the art and pharmaceutically acceptable may be utilized. Examples of the carriers may include saline, distilled water, Ringer's solution, buffered saline, an albumin injection solution, a dextrose solution, a maltodextrin solution, glycerol, ethanol, and the like, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, granules or tablets and the like.

Methods for administering the composition for preventing or treating infectious diseases caused by *Salmonella* according to this embodiment are not particularly limited, and any methods commonly used in the related art may be used. One example of the administration method may include oral administration or parenteral administration of the composition.

Examples of dosage forms for oral administration may include troches, lozenges, tablets, water soluble suspensions, oil-based suspensions, formulated powder, granules, emulsions, hard capsules, soft capsules, syrups, or elixirs, without being limited thereto.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by *Salmonella* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ26 as an active ingredient.

Herein, the term "antibiotics" refers to a preparation that is administered to animals including humans in medicine form and exhibits an effect of killing bacteria, and is used as a general term for antiseptics, germicides and antibacterial agents.

In order to prevent or treat *Salmonella*, many studies regarding vaccines and anti-infective immunity have been actively performed, but over 2500 serotypes of *Salmonella* subspecies reported up to now do not have specific host regions and thus at least one animal is infected or contaminated with such serotypes, it was practically almost impossible to eradicate *Salmonella*.

In addition, *Salmonella* is capable of growing in a phagocyte which intakes bacteria, and thus cannot be treated with antibiotics and even if an animal has no *Salmonella* with use of antibiotics, the animal shows increasing susceptibility of re-infection with *Salmonella* when the administration of antibiotics stops, and thus there is a need for development of antibiotics specifically acting on *Salmonella*.

Antibiotics of this embodiment including the bacteriophage ΦCJ26 as an active ingredient have effects in that the antibiotics have specificity for *Salmonella* as compared with typical antibiotics and thus kill specific pathogenic bacteria, but not beneficial bacteria; and in that the antibiotics do not induce drug resistance, causing extension of lifetime of products as compared with typical antibiotics.

Yet another embodiment of the present invention provides an additive for feeds or drinking water, which includes the bacteriophage ΦCJ26 as an active ingredient.

The additives for feeds or the additives for drinking water may be used by separately preparing additives for feeds or additives for drinking water using the bacteriophage ΦCJ26 or the composition including the same and mixing feeds or drinking water with the additives, or directly adding the bacteriophage ΦCJ26 or the composition including the same in a process of preparing feeds or drinking water.

The bacteriophage ΦCJ26 or the composition including the bacteriophage ΦCJ26 as an active ingredient used in the form of additives for feeds or additives for drinking water according to this embodiment may be a liquid form or a dried form, for example, a dried powder form.

The bacteriophage ΦCJ26 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as *Bacillus subtilis* capable of producing proteases, lipases and/or glycosyltransferase s; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feeds; and yeasts such as *Saccharomyces cerevisiae* and the like. These microorganisms may be used alone or in combination thereof.

The additives for feeds or additives for drinking water according to this embodiment including the bacteriophage ΦCJ26 as an active ingredient may further include other additives as needed.

Examples of usable additives may include binders, emulsifiers, and preservatives added for prevention of quality deterioration of feeds or drinking water; amino acid, vitamin, enzyme, probiotics, flavoring agents, non-protein nitrogen compounds, silicate, buffering agents, coloring agents, extracting agents or oligosaccharides that are added in order to increase utility of feeds or drinking water; and other supplements to feeds, without being limited thereto. These additives may be used alone or in combination thereof.

The additives for feeds according to the present invention may be present in amounts of 0.05 parts by weight to 10 parts by weight, specifically 0.1 parts by weight to 2 parts by weight, based on 100 parts by weight of feed. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ26 against *Salmonella* to be sufficiently displayed.

Yet another embodiment of the present invention provides feeds or drinking water prepared by adding the additives for feeds or the additives for drinking water including the bacteriophage ΦCJ26 as an active ingredient to feeds or drinking water, or directly adding the bacteriophage ΦCJ26 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods, without being limited thereto. These feeds are used alone or in combination thereof.

Drinking water used in this embodiment is not particularly limited, and any drinking water commonly used in the related art may be used.

In addition, the feeds according to this embodiment can be added to drinking water by mixing, and the resultant drinking water can consistently decrease number of intestinal *Salmonella*, which may give a solution to *Salmonella* free livestock production.

Yet another embodiment of the present invention provides disinfectants or detergents including the bacteriophage ΦCJ26 as an active ingredient. Dosage forms of the disinfectants or detergents are not particularly limited, and any dosage forms commonly used in the related art may be used.

In order to remove *Salmonella*, the disinfectants may be sprayed to habitats of animals, slaughterhouses, dead regions, kitchens, and cooking equipment, without being limited thereto.

The detergents may be used to wash a surface of the dermis or body parts of poultry that are exposed to or can be exposed to *Salmonella*, without being limited thereto.

Yet another embodiment of the present invention provides a method for preventing or treating infectious diseases caused by *Salmonella* using the bacteriophage ΦCJ26 or the composition including the bacteriophage ΦCJ26 as an active ingredient.

Specifically, the prevention method or treatment method of this embodiment includes administering a pharmaceutically effective amount of the bacteriophage ΦCJ26 or the composition including the bacteriophage ΦCJ26 as an active ingredient to poultry that are exposed to or can be exposed to *Salmonella*. Suitable total amounts of the bacteriophage ΦCJ26 or the composition including the same per day may be determined by a veterinarian within proper medicinal judgment, as apparent to those skilled in the art.

A concrete pharmaceutically effective amount of the bacteriophage ΦCJ26 or the composition including the bacteriophage ΦCJ26 as an active ingredient to a poultry may be determined by taking into account the sorts and degree of reaction to achieve, age, body weight, general health condition, sex or diet of corresponding individuals, administration time and administration routes of bacteriophage ΦCJ26 or a composition including the same, and secretion rate of the composition, treatment period, and the like, and may differ depending upon various factors and similar factors well known in the field of medicine including ingredients of medicines that are used simultaneously or at different times.

The bacteriophage ΦCJ26 or the composition including the bacteriophage ΦCJ26 as an active ingredient may be administered in the form of pharmaceutical preparation to birds by intranasal spraying, or directly added to avian feeds or drinking water so as to be digested, and may be mixed in the form of additives for feeds or additives for drinking water with feeds or drinking water and then administered.

Routes and methods for administration of the bacteriophage ΦCJ26 or the composition including the bacteriophage ΦCJ26 as an active ingredient are not particularly limited, and the administration may be realized by any routes and methods so long as the administration allows the bacteriophage ΦCJ26 or the composition including the same to reach desired tissues.

Namely, the bacteriophage ΦCJ26 or the composition including the bacteriophage ΦCJ26 as an active ingredient may be administered by various oral or parenteral routes, and examples of administration may include oral, rectal, topical, intravenous, intraperitoneal, intramuscular, intra-arterial, trans-dermal, intranasal, or inhalation, without being limited thereto.

Hereinafter, the present invention will be described in more detail with reference to some examples. It should be understood that these examples are not to be construed in any way as limiting the present invention.

[Example 1]—Isolation of Bacteriophage that Infects *Salmonella*

Example 1-1

Bacteriophage Screening and Single Bacteriophage Isolation 50 ml of a specimen obtained from chicken feces collected around a poultry farm in Gwangcheon, Hongsung-gun, Chungcheong Province was centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}$=2) of *Salmonella senftenberg* (SS) obtained from the Department of Veterinary Medicine of Konkuk University and 2 ml of 10×LB medium (10 g/l of tryptophan; 5 g/l of yeast extract; 10 g/l of NaCl) were mixed with 18 ml of the filtered specimen liquid, followed by culturing at 37° C. for 18 hours, and the resulting cultured solution was centrifuged at 4,000 rpm for 10 minutes, and the resulting supernatant was filtered through a 0.45 μm filter. Subsequently, a mixed solution consisting of 3 ml of 0.7% (w/v) agar and 150 μl of a shaking culture solution ($OD_{600}$=2) of SS was poured and solidified on an LB medium plate, to which 10 μl of the specimen liquid was added dropwise, followed by culturing at 37° C. for 18 hours, thereby identifying formation of plaques.

Since it is known that one sort of bacteriophage is present per plaque, the inventors tried to isolate single bacteriophages from the formed plaques. Specifically, 400 μl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution.

Next, 100 μl of the bacteriophage solution was mixed with 12 ml of 0.7% (w/v) agar and 500 μl of a shaking culture solution ($OD_{600}$=2) of SS, which was used to perform a soft agar overlay method using an LB medium plate having a diameter of 150 mm wherein cultivation was performed until the bacteriophage was completely lysed. After completion of cultivation, 15 ml of SM solution was added to the LB medium plate and left at room temperature for 4 hours, thereby obtaining a bacteriophage solution.

To the solution, 1% (v/v) chloroform was added and mixed for 10 minutes, followed by centrifugation at 4,000 rpm for 10 minutes, thereby obtaining a supernatant, which in turn was filtered through a 0.45 μm filter to obtain a final specimen.

Example 1-2

Large Scale Culture and Purification of Bacteriophage

Bacteriophage obtained in Example 1-1 was cultured at large scale using *Salmonella senftenberg* (SS), and then the bacteriophage was purified therefrom.

Specifically, SS was shaking cultured, and inoculated at $1.5 \times 10^{10}$ cfu, followed by centrifuging at 4,000 rpm for 10 minutes, and re-suspending in 4 ml of SM solution. To this, the bacteriophage was added at $1.5 \times 10^8$ pfu with multiplicity of infection (MOI) of 0.0001, and then left at room temperature for 20 minutes.

Next, 150 ml of LB medium was inoculated therewith, and cultured at 37° C. for 6 hours. After completion of cultivation, chloroform was added to a volume of 1% (v/v) of the final volume, followed by stirring for 20 minutes, to which DNase I and RNase A as restriction enzymes were added in a final concentration of 1 μg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 4 ml of chloroform was added thereto with stirring, followed by centrifugation at 4° C. with 4,000 rpm for 20 minutes, thereby obtaining a supernatant. The supernatant was filtered through a 0.45 vim filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill *Salmonella* from samples collected from chicken feces on farms, which was designated as "Bacteriophage ΦCJ26" and deposited at the Korean Culture Center of Microorganisms (KCCM) (361-221 Hongje 1-dong, Seodaemun-gu, Seoul, Korea) on Oct. 25, 2013 under accession number KCCM 11464P.

Example 2

Morphology Observation of ΦCJ26

The bacteriophage ΦCJ26 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water.

Subsequently, the carbon film was mounted on a copper grid, and stained with 4% uranyl acetate for 60 seconds, dried, and examined under a transmission electron microscope (JEM-1011, 80 kV, magnification of 200,000×) (FIG. 1).

FIG. 1 is a transmission electron microscope image of bacteriophage ΦCJ26, in which the bacteriophage ΦCJ26 had morphological characteristics of an icosahedral capsid with a long non-contractile tail, indicating that the bacteriophage belongs to morphotype Siphoviridae.

Example 3

Total Genomic DNA Size Analysis of ΦCJ26

Genomic DNA was extracted from the bacteriophage ΦCJ26 purified in Example 1.

Specifically, to a cultured solution of the purified bacteriophage CJ26, 20 mM ethylenediaminetetraacetic acid (EDTA), 50 μg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol:chloroform=1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 3M sodium acetate in an amount of 10% (v/v) based on the total volume, followed by addition of 2 volumes of 95% cold ethanol, mixing, and standing at −20° C. for 1 hour.

Subsequently, the resulting substance was centrifuged at 0° C. and 12,000 rpm for 10 minutes, from which a supernatant was removed to obtain a precipitate, which was dissolved in 50 µl of TE buffered solution (Tris-EDTA, pH 8.0). The extracted DNA was diluted 10 fold, and then concentration of DNA was determined by measuring absorbance at $OD_{260}$.

Next, 1 µg of DNA was loaded on a 1% PFGE (pulsed field gel electrophoresis) agarose gel, and developed using BIORAD PFGE SYSTEM NO.7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ26, and it could be seen that the genomic DNA size of the bacteriophage ΦCJ26 was about 90 kbp.

Example 4

Protein Pattern Analysis of ΦCJ26

15 µl of purified bacteriophage ΦCJ26 solution ($10^{11}$ pfu/ml titer) was mixed with 3 µl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ26, and it could be seen that main proteins had a size of about 12.1 kDa, about 16.4 kDa, about 44 kDa, and about 54 kDa.

Example 5

Analysis of Genetic Properties of ΦCJ26

In order to determine genetic properties of the bacteriophage ΦCJ26 purified in Example 1, DNA of the bacteriophage ΦCJ26 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan program.

Nucleotide sequence of the bacteriophage ΦCJ26 showed similarity to nucleotide sequence of previously reported bacteriophages (*Salmonella* phage SPT-, *Escherichia* phage EC6, *Staphylococcus* phage SA1), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ26 and decoded nucleotide sequence of the bacteriophage reported in the art.

TABLE 1

| Query | | | | Subject | E-Value | Identities Match/Total | Pct. (%) |
|---|---|---|---|---|---|---|---|
| Name | Length | Start | End | Description | | | |
| SEQ ID NO: 1 | 47188 | 8892 | 21376 | *Salmonella* phage SPT-1, partial genome | 0 | 11725/ 12516 | 93 |

TABLE 1-continued

| Query | | | | Subject | E-Value | Identities Match/Total | Pct. (%) |
|---|---|---|---|---|---|---|---|
| Name | Length | Start | End | Description | | | |
| SEQ ID NO: 2 | 20949 | 10291 | 20949 | *Escherichia* phage EC6, complete genome | 0 | 10106/ 10683 | 94 |
| SEQ ID NO: 3 | 18448 | 1 | 17009 | *Staphylococcus* phage SA1, complete genome | 0 | 16257/ 17037 | 95 |

DNA of the prepared bacteriophage ΦCJ26 was analyzed using a DNA sequencer and partial results of the analyzed nucleotide sequence are set forth in SEQ ID NOs: 1 to 3.

Example 6 pH Stability of ΦCJ26

In order to identify whether the bacteriophage ΦCJ26 can maintain stability at low pH like stomach conditions, stability of the bacteriophage ΦCJ26 was examined at various pH (pH 3.0, 4.0, 5.0, and 5.5).

For the experiment, various pH solutions (sodium acetate buffer solutions (pH 4.0, pH 4.5, pH 5.0, pH 5.5) and sodium citrate buffer solutions (pH 3.0)) were prepared at a concentration of 0.2M.

180 µl of each pH solution was mixed with 20 µl of a bacteriophage solution with $10^8$ PFU/ml titer until each pH solution had a concentration of 1M, and then the resulting solution was left at room temperature for 2 hours. For a control group, 20 µl of a bacteriophage solution with $10^8$ PFU/ml titer was mixed with 180 µl of SM solution by the same method, and the resulting solution was left at room temperature for 2 hours. Thereafter, the solutions were serially diluted, and 10 µl of each of solutions in each dilution step was cultured by the soft agar overlay method at 37° C. for 18 hours to determine bacteriophage titer based on whether the bacteriophage was lysed (FIG. 4).

FIG. 4 shows experimental results of acid resistance of the bacteriophage ΦCJ26. In FIG. 4, it could be seen that the bacteriophage ΦCJ26 did not lose its activity and maintained stability from pH 4 to pH 5.5, as compared with the control group.

Example 7

Heat stability of bacteriophage ΦCJ26

If bacteriophages are formulated into additives for feeds among dosage forms of bacteriophages, heat can be generated during formulation procedures, and thus, the following experiment was performed in order to determine heat stability of bacteriophages.

Specifically, 200 µl of bacteriophage ΦCJ26 solution with $10^8$ PFU/ml was left at 60° C. for 10 minutes, 30 minutes, 60 minutes and 120 minutes, respectively. Thereafter, the resulting experimental culture solution was serially diluted, 10 µl of each of solutions in each dilution step was cultured by the soft agar overlay method at 37° C. for 18 hours to determine bacteriophage titer based on whether the bacteriophage was lysed (FIG. 5).

FIG. 5 shows experimental results of heat resistance of bacteriophage ΦCJ26. As shown in FIG. 5, it could be seen that bacteriophage ΦCJ26 showed no activity decline until bacteriophage ΦCJ26 was exposed to 60° C. for 120 minutes.

Example 8

Drying Stability of Bacteriophage ΦCJ26

If bacteriophages are formulated into additives for feeds among dosage forms of bacteriophages, bacteriophages can be dried during formulation procedures, and thus, the following experiment was performed in order to determine stability of bacteriophages against drying conditions.

Based on the results of a heat resistance experiment, drying experiment was performed using a SpeedVac concentrator. 200 μl of bacteriophage ΦCJ26 solution with $10^8$ PFU/ml was dried at 60° C. under vacuum for 2 hours, and the resulting pellets were introduced to 200 μl of SM solution, followed by completely re-suspending at 4° C. for one day, thereby measuring titers (FIG. 6).

As shown in FIG. 6, it could be seen that, after drying, as compared with initial titers and relative stability, bacteriophage ΦCJ26 showed activity decline of about 1 log when bacteriophage ΦCJ26 was dried at 60° C. for 2 hours.

Example 9

Examination of Infection Range of Bacteriophage ΦCJ26 on Wild-Type Isolated Strains of *Salmonella*

Lytic activity of bacteriophage ΦCJ26 was tested for 9 strains of the wild-type *Salmonella sentfenberg*, 14 strains of *Salmonella montevideo*, 12 strains of *Salmonella newport*, 10 strains of *Salmonella Kentucky*, 13 strains of *Salmonella mbandaka*, 11 strains of *Salmonella infantis*, 4 strains of *Salmonella handar*, 5 strains of *Salmonella derby*, 4 strains of *Salmonella sholeraesuis*, and 13 strains of *Salmonella Thomson*, which were all isolated from a farm run by the College of Veterinary Medicine, Konkuk University (KU), in addition to *Salmonella senftenberg* used in the present experiment.

Specifically, 150 μl of a shaking culture solution of each strain ($OD_{600}=2$) was mixed, and 10 μl of bacteriophage ΦCJ26 solution with $10^9$ pfu/ml titer was dropped thereto and cultured by the soft agar overlay method at 37° C. for 18 hours, and then plaque formation was examined (Tables 2 and 3).

The results are shown in Tables 2 and 3.

TABLE 2

| *Salmonella* | Strain | ΦCJ26 Plaque formation | *Salmonella* | Strain | ΦCJ26 Plaque formation |
|---|---|---|---|---|---|
| S. senftenberg | 8-Senftenberg | ○ | S. Kentucky | Kentucky 1 | ○ |
| | 10-Senftenberg | ○ | | Kentucky 2 | ○ |
| | 11-Senftenberg | ○ | | Kentucky 4 | ○ |
| | 21-Senftenberg | ○ | | Kentucky 5 | ○ |
| | 51-Senftenberg | ○ | | Kentucky 6 | ○ |
| | 94-Senftenberg | ○ | | Kentucky 7 | ○ |
| | 95-Senftenberg | ○ | | Kentucky 12 | ○ |
| | 130-Senftenberg | ○ | | Kentucky 13 | ○ |
| | 530-Sal. Senftenberg | ○ | | Kentucky 14 | ○ |
| S. montevideo | 5-Montevideo | ○ | | Kentucky 15 | ○ |
| | 13-Montevideo | ○ | S. mbandaka | S. mbandaka B09-046 | ○ |
| | 14-Montevideo | ○ | | S. mbandaka B09-047 | ○ |
| | 15-Montevideo | ○ | | S. mbandaka B09-069 | ○ |
| | 17-Montevideo | ○ | | S. mbandaka B09-101 | ○ |
| | 16-Montevideo | ○ | | 22-Mbandaka | ○ |
| | 18-Montevideo | ○ | | 23-Mbandaka | ○ |
| | 122-Montevideo | ○ | | 32-Mbandaka | ○ |
| | 123-Montevideo | ○ | | 34-Mbandaka | ○ |
| | 150-Montevideo | ○ | | 35-Mbandaka | ○ |
| | 533-Sal. Montevideo | ○ | | 29-Mbandaka | ○ |
| | 582-Sal. Montevideo | ○ | | 36-Mbandaka | ○ |
| | 600-Sal. Montevideo | ○ | | 30-Mbandaka | ○ |
| | 621-Sal. Montevideo | ○ | | 31-Mbandaka | ○ |
| S. newport | *Salmonella* Newport SARB36 | ○ | S. infantis | *Salmonella* Infantis SARB26 | ○ |
| | *Salmonella* Newport SARB37 | ○ | | *Salmonella* Infantis SARB27 | ○ |
| | *Salmonella* Newport SARB38 | ○ | | *Salmonella* Infantis S1326/28 | ○ |
| | *Salmonella* Newport 7257 | ○ | | S. Infantis B09-106 | ○ |
| | *Salmonella* Newport SL254 | ○ | | 77-Infantis | ○ |
| | *Salmonella* Newport SL317 | ○ | | 82-Infantis | ○ |
| | 3-Newport | ○ | | 136-Infantis | ○ |
| | 38-Newport | ○ | | 172-Infantits | ○ |
| | 39-Newport | ○ | | 528-Sal. Infantis | ○ |
| | 106-Newport | ○ | | 537-Sal. Infantis | ○ |
| | 127-Newport | ○ | | 571-Sal. Infantis | ○○ |
| | 128-Newport | ○ | | | |

TABLE 3

| S. thompson | Thompson 1 | ○ | S. hadar | 98-Hadar | ○ |
| --- | --- | --- | --- | --- | --- |
| | Thompson 3 | ○ | | 126-Hadar | ○ |
| | Thompson 4 | ○ | | 575-Sal. Hadar | ○ |
| | Thompson 5 | ○ | | 576-Sal. Hadar | |
| | Thompson 6 | ○ | S. derby | S. Derby B09-033 | ○ |
| | Thompson 7 | ○ | | S. Derby B09-041 | ○ |
| | Thompson 8 | ○ | | S. Derby B09-061 | ○ |
| | Thompson10 | ○ | | S. Derby B09-062 | ○ |
| | 114-Thompson | ○ | | S. Derby B09-063 | ○ |
| | 115-Thompson | ○ | S. cholerasuis | Salmonella choleraesuis 2930 | ○ |
| | 118-Thompson | ○ | | Salmonella choleraesuis 2929 | ○ |

TABLE 3-continued

| | 120-Thompson | ○ | | Salmonella choleraesuis SNU #1 | ○ |
| --- | --- | --- | --- | --- | --- |
| | 121-Thompson | ○ | | Salmonella choleraesuis SNU #2 | ○ |

As shown in tables 2 and 3, the bacteriophage ΦCJ26 can infect *Salmonella senftenberg, Salmonella Montevideo, Salmonella Newport, Salmonella Kentucky, Salmonella mabandaka, Salmonella infantis, Salmonella handar, Salmonella derby, Salmonella choleraesuis, Salmonella Thomson* and the like, which are major causative bacteria of infectious diseases caused by *Salmonella* in general poultry farms.

Sequence List Fee Text

Submitted by attaching SEQUENCE LIST

The invention claimed is:

1. A feed composition comprising a feed and an additive comprising bacteriophage ΦCJ26 deposited as accession number KCCM11464P.

2. A drinking water composition comprising drinking water and an additive comprising bacteriophage ΦCJ26 deposited as accession number KCCM11464P.

3. A method for preventing or treating infectious diseases caused by *Salmonella*, comprising:
administering bacteriophage ΦCJ26 deposited as accession number KCCM11464P to a non-human animal.

4. The method for preventing or treating infectious diseases caused by *Salmonella* according to claim 3, wherein the animal is poultry.

5. A method for preventing or treating infectious diseases caused by *Salmonella*, comprising:
administering a composition comprising bacteriophage ΦCJ26 deposited as accession number KCCM11464P to a non-human animal.

6. A method of preparing an additive composition, the method comprising:
providing bacteriophage ΦCJ26 deposited as accession number KCCM11464P; and
mixing the bacteriophage with at least one additional material to provide the additive composition.

7. The method of claim 6, wherein the bacteriophage is in an amount of 0.05 wt % to 10 wt % based on the weight of the additive composition.

8. A method of preparing a feed composition, the method comprising;
preparing an additive composition according to the method of claim 6; and
mixing the additive composition with an animal feed to provide the feed composition.

9. A method of feeding, the method comprising:
preparing the feed composition according to the method of claim 8; and
providing the feed composition to an animal.

10. A method of preparing a drinking water composition, the method comprising:
preparing an additive composition according to the method of claim 6; and
mixing the additive composition with drinking water to provide the drinking water composition.

11. A method of providing drinking water to an animal, the method comprising:
preparing the drinking water composition according to the method of claim 10; and
providing the drinking water composition to an animal.

* * * * *

UNITED STATES PATENT AND TRADEMARK OFFICE
CERTIFICATE OF CORRECTION

PATENT NO. : 9,956,256 B2  
APPLICATION NO. : 15/304429  
DATED : May 1, 2018  
INVENTOR(S) : Eun Mi Shin et al.

Page 1 of 2

It is certified that error appears in the above-identified patent and that said Letters Patent is hereby corrected as shown below:

On the Title Page

Item (*) Line 3, after "0 days." Delete "days.".

In the Specification

Column 1, Line 57, change "*Chlorstridium.*" to --*Clostridium*.--.

Column 3, Line 20, change "*@CJ26.*" to --*ΦCJ26*.--.

Column 3, Line 50, change "*abortusovi,*" to --*abortusovis*,--.

Column 3, Line 52, change "*Thomson,*" to --*Thompson*,--.

Column 3, Line 62, change "*hader,*" to --*hadar*,--.

Column 3, Line 63, change "*thomson*" to --*Thompson*--.

Column 4, Line 61, change "*the term "treating""* or" to --*the term "treating"* or--.

Column 9, Lines 9-10, change "*Hongsung-gun,*" to --*Hongseong-gun*,--.

Column 10, Line 15, change "*vim*" to --*μm*--.

Column 10, Line 53, change "*CJ26,*" to --*ΦCJ26*,--.

Column 11, Line 12, change "*NO.7*" to --*NO. 7*--.

Column 14, Line 6, change "*sentfenberg,*" to --*senftenberg*,--.

Signed and Sealed this  
Eighteenth Day of September, 2018

Andrei Iancu  
*Director of the United States Patent and Trademark Office*

CERTIFICATE OF CORRECTION (continued)
U.S. Pat. No. 9,956,256 B2

Column 14, Line 10, change "*handar,*" to --*hadar,*--.

Column 14, Line 11, change "*sholeraesuis,*" to --*choleraesuis,*--.

Column 14, Line 12, change "*Thomson,*" to --*Thompson*--.

Column 13-14, Line 14 of Table 2, change "*mbandaka*" to --*Mbandaka*--.

Column 13-14, Line 16 of Table 2, change "*mbandaka*" to --*Mbandaka*--.

Column 13-14, Line 18 of Table 2, change "*mbandaka*" to --*Mbandaka*--.

Column 13-14, Line 20 of Table 2, change "*mbandaka*" to --*Mbandaka*--.

Column 13-14, Line 44 of Table 2, change "*172-Infantits*" to --*172-Infantis*--.

Column 15, Line 12 of Table 3, change "*cholerasuis*" to --*choleraesuis*--.

Column 16, Line 11-12, change "*mabandaka,*" to --*mbandaka,*--.

Column 16, Line 12, change "*handar,*" to --*hadar,*--.

Column 16, Line 13, change "*Thomson*" to --*Thompson*--.

```
SEQUENCE LISTING

<160> NUMBER OF SEQ ID NOS: 3

<210> SEQ ID NO 1
<211> LENGTH: 47188
<212> TYPE: DNA
<213> ORGANISM: Artificial Sequence
<220> FEATURE:
<223> OTHER INFORMATION: Novel Bacteriophage CJ26

<400> SEQUENCE: 1
tttaaagcgt cttgcagatg ttgagaagcg tactggtcaa gagtgtatca tcagaatgtc      60
agtggttgat ggtaaagagt ggtatgcgat tgtccgtgca gcagatggga agattatgaa     120
gcaatcaaat ctccctaaag tacagcttgg tgaatacatt gtagagcttg aaagccaaga     180
actttttgtg gtagtatctg agacatgcgt tatctgcaaa ggtattgtag gtagcttaaa     240
ggatttgggt gtagatggtt ttgtagaagt taatccaatt acctctaaag cagataaaga     300
tttctgtaaa gagaatggac tatggattgc agatattgtc tactacgatg gtgagcagtt     360
ccatgtaacc tcataccga aactgaatta tgatgctaat aacctgaagt gctggttaaa     420
aggggttggt tataatggat tcacagaaca ttaataaaga aggtgtggct cagaagagcc     480
acttctcaaa ctacaatatc tctatgacgg tgtttatgta tgacccgtta cttgagaagt     540
atggtgagac tccagataca cttctggata atgaacaagt tttaaaagca gttctgtaca     600
aatacgggat tgatattgag aaagagtatt cttttgaaat ctgtcaacac aggaatactt     660
ttggtaaagt tgtaatggct ccactcttca tgggtgtaga aagaactgac tatggttggt     720
tatatctaaa aagaaacttg gagaaatacc gtgtctaaag caaaaaagct atcttatgat     780
gacattatct caggtgctaa attaggtgtt gatagtatcg gacaagatgt taagcacgga     840
gacacagtta tgtactgtga tgaccgaaga gggagaagtg caatcttgtt tggaagaatt     900
gtttgcaaga tgcgaggtaa ttacgttgtt gcagacatgg atgtgaacgt tacacaaaaa     960
cttgaaacac ttatggatga taatacatca tcatggttct ccctgaattg tatgcacact    1020
tcttcagtca caaagtaag  tgataagttt tacgatatgt ggcagaatga gcaaatttc    1080 aagatttaaa ctagggagcc tcttcggagg ctcttttcat ctgtaggatt caaaaatgat    1140
taagacaatt aaaaaatcaa acggtacagt agtaaacttt gacccagaaa gactgaataa    1200
gtgggcatca tgggcagata agcgtggtat tatctggtca gaagtcacta tggaagccat    1260
gaaacgtgtc tatgaaggtt gcactacaaa agagatgcac caagccatga ttgatgtttg    1320
tgttgataaa caaactcaag agtactcaga catggctgga cggctacttc tgggattat    1380
```

-continued

```
ctacaaagaa gcctttggag gctttactaa ggttcctacg ctggttacct tcgttaaaaa    1440
tatggagaga gcaggacttt gggagaagat ggactattct caggaagagc ttgaatatct    1500
gcaagggtac attgtgcact caaaagatat ctcttacggt tatgcagtct gaaacagtt    1560
cagagacaag tatggtatcc gtgatattaa aacgggaaga cttttgagt caccgcagtt    1620
tatgtttatg ggtatggcta tgaaagcctt cgagaagcaa ccaaagcacc gtagactgca    1680
agatgttatc aagctgtaca cttacctatc tgacctgaag attaatgctc ctacaccta    1740
tctgaatggt ttaagagcta ctaaatcagg ttacgcgtca tgctgtttga ttaaggcaaa    1800
tgatactgct gaatcacttg gtattgctgc aaaggttgct tatgatatga ctacaaagca    1860
agctggtatt gggatgctga tggagactcg tactattggt gatggtatcc gtcaaaatac    1920
tattgagcac atgggtaaac taccttatta caagcttgta cgttcatctg tagaggcaaa    1980
caaacagaag agccgtggtg gttcagctaa caacttctac actgctctag acccacagat    2040
tgaagattta ctgcgtttga agcaccctac aacggttcct tcgaaacgta ttaacgagat    2100
ggactactca tttggtacaa atgattactt ctggcagtgt gttcaatatg atacagactg    2160
gttgttattc tcttacaagg atgcaccaaa gctctatgac atgttctaca cagcatctgc    2220
tgatgagttt gctatggcag ttggtcatgc agtgcattca ggtgttaagc acagacgagt    2280
aaaggctcgt gaaattgcta aactgtttat ccagcagcgt tatgcaacag gacgtgtgta    2340
tccattcttc acaaataatg caaacacaca taccacattt aaagagcctt tgaagatgtc    2400
aaatctttgt atggaaatcg tgttgccagt gtatggattt gagaaggaga cagaccttta    2460
cagagacgat gctgtgaaag aggatggtga ggtagctctt tgcttcctag ctagtttggt    2520
tgcagggaga atttcagaag atgaatacgc tgacgttgct tattatgctc ttgcaatggt    2580
tgactccgtt attgacctta tggattatcc gtatccctcg atgcgcaacc atgttcagaa    2640
gcgtcgttct gttggtattg gccttacaaa tgtggctcat tacttgcga aaaactacgt    2700
gaactactct tcaagagcag gtaagacaaa gctccatgag cttgctgaaa tgcactctta    2760
ctacttacac gaagcctctt taagacttgc taaagaacgt ggtgtgcctg agtatatgca    2820
gttcactaag tatcctgaag gttgggttcc tccgaagaca gctaacagga agattgatga    2880
gaagcatgat gcaaaacttc gttatgattg ggatgactta gcacaacgta ttaaagaaaa    2940
tggtggaatc cgtaactctg tattagaggc ttacatgcct aatgagagtt cttcactggc    3000
aactaatacg caaatggct tgtatccaat tcgtgacttt atttaacta aaaagtctgc    3060
aactggtaac gtactgttta ttgttccaga ttacgaagag ttgaagtatg tctatgaaat    3120
tgcttgggat attgacacct ttgacctgat tgattgttat gcaattgttc aaaagttcac    3180
tggtcaagct atctcttcag atttctatgt tgactatgca aagtctaaga aggtatcatt    3240
ggctcaagct ttgaagtata tgatttatgc caactcagtc ggtatgaaaa ccatgtacta    3300
tctcaacagc cgcattggtg taggtaagtc tgcactgcaa gatgcttatt gcagggttg    3360
tggtgtttag ttttaataac tatgagggtc gtaaaagacc ctctaaaatt aactttggag    3420
agactatgaa agacttaata gcaaatcacg aatggcccat atacttgctc cacaaacctc    3480
ggaaaacgat gtactatgtg agtagcacag acatgatgat aaaacaaaat gatgactcat    3540
gggtcgatgg tgtctcttac atctctacag cagatggtaa aatctatgca agaccttatg    3600
acatgtttaa caaagaaaat tgggaagttt tagacagaaa acaagcctta gagatgataa    3660
agaaaggaga aatcacgcta tgattaacca acacccaatc ttttaggtg gtgagaggaa    3720
```

```
gacatttgac tcacttaaca agcactaccc aaaaatcttt gaactctata acaacaaaa    3780
agcacaagac tggtcagaag atgagttccc ttttgaacaa tcacgtcttg attttgagag    3840
tgtaccagca tcaatgtcag gtgtaatgct tgagattctt aagtggcagt gggaagcaga    3900
tacccaagtt gctaagagtt tagcgtttgc ttttgcacca ttcatctctg atgacattta    3960
tgcaactgca attatgaagc agtctgagat tgaaaaccta catgctctta cttactcgga    4020
gattgtaaga cagtgtatta aaaatcctga acaatctta  gatgagatta accagaacat    4080
tgctgtacaa gaccgattaa aaactgtgaa tcgtgttctt gaagaattac tggatgaagg    4140
tataaactat cgactgagtt atgtccgtga ctcacttctg gataaagacc ctttgcactt    4200
ccataaagtg attctaaaag gtctatttgc agtgactgca ctggaaggta tatcttttat    4260
ggcatccttt gcatgtactt ttgcactcga tgctcaagat aaatttcagg gtattgctca    4320
agctgtccag aaaattatgc ttgatgaaac ccttcacact aaaattgata ttgaagtttt    4380
aaaagaaact ttaagagatg atgagtggca aaaagctttc caacaaattc ttccagagat    4440
taaagtaatc ttagatgaag tagttgaaag tgaagaaaaa tggtcgtatt atatcttctc    4500
cgaaggacgt gctgtagttg gtttaaatac aaagcttctt catgagtggg tttactataa    4560
tgctgcccca ctgtatgata tgtttggcat tcccagagat tttgtagctc ctaaagaacc    4620
acctttgaag tatatgatta agaagatgga aattgataaa gagcagaatg ctaatcagga    4680
gcaacagaac ggtgcgtatt tattgaatac tgttgtcgat gatttgaata gtggattttt    4740
agaggttcct taatgactta tgtaatttac tccaaaactg gatgccctca gtgtgagact    4800
gcaaagaatt ttgcaaaagc tcgtggtatt gaccatgttg tgagaatgtt agggcaggat    4860
tatgaactgt cagacctgat ggatattgca cagatgccag ttcgtcagat gccattcatc    4920
atgaaaactg atggtcaaaa tctaaaacct gttggaacgc tacagaattt tatggcagag    4980
gtgaataatg cttaaacgcc tttgggaagg cttggttgtt gatgcaccag ccattgtgat    5040
tggtatgctt attgttaacc tatttactga ttttgaacaa ggttcattgt ttggagccat    5100
gttactatgg gttatctttg aaatattaga gatacagcta ggcatcactg aaaaactaag    5160
aaaactcgtt tcaaagtttt ctaaaaagat ttaaaatgaa agggtctctt cggagacctt    5220
tttagcatgt aaaggggcaa taatgaacaa agtacagatt attaaaaaga atggctcact    5280
tgaagaacct gatatcaaaa aagttttagc agcagtaact aagtcagcta acagggttgg    5340
gtataaagaa cttccaccag atgttaccca agctcttgag tcagcattta tgaggattct    5400
ggtaaagtcc actaagcaga acaatttgct catctcggta aatgacattc atagtattgt    5460
tgagggtgct ttggcagaag tcaatcacga gatttatgag tcttactcaa catatagaaa    5520
ttaccgtaaa gaagttgctc aaaattggga tgaactctac cagaagacca agatacact     5580
cttcttaggt gacagagaga atgctaactt tgacagcagt ttaatttcta caaaaggttc    5640
aattattcgt ggttatctga ctaaagaaat ctttaaacag taccacttaa caccagagga    5700
acttgaagcc attgaaaaag ggtttatcta tatccatgat ttaagagacc taattttgg    5760
tggtatcaac tgttgcctgt ttgacattgg taaagtcctg aaaggtggct ttgaaatgtc    5820
tggcattgaa tattgtgaac cgaagtctgt actatcagcc ttcaggtta ttggtgacgt     5880
agttctttca gcaactgcac agcaatttgg tggctttact ttagcagaga ttgataaggt    5940
acttgtgccg tatgctaaga agtctctacg ctatcatgct gagaaagcag catcttacgg    6000
tattcctaaa gaacattacc acaattatgt catggagcag ctacagattg aactgactca    6060
aggtttccag tcacttgaaa tgaaactaaa cactgtacct tgtagtcgtg gggatttgc     6120
```

```
atttacaact tgacattcg ggttacttga ctcagatatg tccaatgaag ataaccgact    6180
acaatacatg attgcaagca ctctcctaga tgttcgtatg aatggacaag gtaagagcaa    6240
gaaacctgtt gtattcccta aactggttta tatttatgac cagaagagac acgatgagaa    6300
tatctgtcaa ggacacctgt acagtaaagc tatagagtgt tgctctaaag cgatgtatcc    6360
agatttctta agtgtatctg gtcatggtgc tgtagcagag gcttttgagc gttctggtaa    6420
ggtgatttca ccgatgggtt aataagctct atagctcatc taaaacgtgc ctaaacaggg    6480
aaactctaca ggtgtagaca atcctgtgct aaatgatgta cgatgtaaga aactatataa    6540
aataggagta ttcatgcca aattatcatg ttactgagga cggaagagtc tttaggaaaa    6600
atggtgtaga acttacgcag tggaaatcca acactggtta tatgaaagta aggttttatg    6660
gaaggaagaa tcgtgacatg tatgtccata ggttagttgc tgaaaagtat gtacctaacc    6720
ctaacaatct tccaattgta aaacacaaag atgataacaa actgaacaac catgcttcta    6780
acttagaatg gggaactcat tctgagaatg ttaaagaagg ctatgagaat ggttgctaca    6840
agttttgtaa gcgttcatat gctgtgaagg ctacacataa agtgacaaaa gaagttattg    6900
ttgctaagtc aatacgagag ttatctaatg tacttgggta taatcgcaag actatctctt    6960
caatattgaa gggtgtaaaa gagtataata actttgaaca tgattttgag tacatttaaa    7020
tgccgaacga ctaaccgtga tgaatgtagc ggtgtagggt caagcgactc gaaatggtac    7080
gctacttaga aataagtaga agatatagtc tggacttact ggtgacagta agcagcttga    7140
ataaagcggg gtaagcgtag cgaacttacc tgaacaacaa gtgtagagcg ttttatcac    7200 catatcataa cgaagatggt gaagagtttt atgtaggtcg tgctaacatt ggtgctgtat    7260
cttgaacttt accaatgatt taccagtatt ctaaagagaa tggtttagat ttctggaaag    7320
agcttgataa gtacctagag atgattcgca gcttccacaa gaaacgctac gaaatgattg    7380
ctaatatgcc agcaagttct aaccctcttg cattcacaca aggtggtctg tacaaaggaa    7440
ctaagaaacc tactgacaag gttggttggg atatcgtgaa gtccttcaca gcttcttttg    7500
gggttactgc tcttgatgag ctgtctgttc ttgctgaagg taaacgactt catgaagttg    7560
gaagctacag ttttgcatac gatgttctgg catacattaa catgaaaact gaagagttta    7620
agaatgaaga tggcttcctg tatgcagtat atggcactcc agcagagtca ttgtgtggaa    7680
ctcagctaaa acagttcaga gatatgtttg gcgttattaa aggtgtttct gataaggaat    7740
actttacaaa cagcttccat atgaatgttg cagcagatat ctcaccattt gagaagcagg    7800
acttagaaga accattcttc catatctgta gaggtggtag aatccagtat gtgagggtag    7860
ctaacccaga aaacttacca gcacttaaaa gttgtattac agggggatg ttgaaaggct    7920 tttatcaggg acttaacttt gacttagcaa tctgtgagca ttgtggtaac aggccaaaag    7980
ctgatgtcga agaatgtgag gtttgccatt cacatgacat ctctgtgatt aacagggtgt    8040
gcgggtactt gtcattcaca aaaattaaag gccagtctcg aatgaatgac gctaagatgg    8100
cagaaattaa ggataggatt ctatgtaaa acttgacaag gtggtgtgag tcttgatagg    8160
cttacatcac ctttttttatt ggatgttaga catggcagag agtattattg ggttgttcat    8220
aggttctgtc ttactagggt tcttttagga cttttcttatt gtgaattgag agataagtta    8280
aatgtttaaa ataccaaaaa cgttgatata catactccac actctaatct tcttctttgg    8340
ggttagtgtt atggtatgga gttttttcaga cccacaatgg agtttatcat atcatggaca    8400 aatggatttta tggtcatgct tcaaaccatt tttagggtta gccatagcat tcagtgcatt    8460
```

```
accaactagg gtgaaattat gattaagttg aaccaaaaac agttagagtg ggttaaagac      8520
tacgcctcag agtgtggctc ttgcgaaaag aatcacgtaa aatactcaac attccataca      8580
gtcttcacat tgtacatcag cgacaatgtt ctaagtgatt ccgtagaaga cggtgtagcg      8640
ttgcctaatg agttacttga taaactagct gtagtcactg gaacttggtc tgaagaagat      8700
ggtcacgaac tctctgatga tgttgtcttc tacactcttg aaaacattat gaatccagag      8760
tacattatgc taatgacttg tgcacaagac tgtgttccat tacaaaactt cattaaagaa      8820
cactgtgaag aatttattac taaacaggtt ccttgtcagg tagtgtttga atgagtaaaa      8880
caattaaata atattggtga ggtaaataga tgaattacat ggagattcga ccatttgaca      8940
cagctaatgg tgaaggggtt cgggtaagcc tcttcgtagc tggctgtaaa catcactgtg      9000
aaggctgctt aacagggag tcttggaagt ttaatgctgg taaagagttt acttatgcaa       9060
acctctacgg catcattaaa ttaatggatg atgaggccat cagtgggttg tcaatgcttg      9120
gtggagaacc tctggatgac agaaacattc gagaggtcac caacatatgc aagcgtatta      9180
aaactgttta tccagaaaag tctatatggc tttggacagg ttttcaacta cacgaaaaaa      9240
tccacttaga tgttatgaaa tatgttgacg tggttattga tggtaagtat gattcttcta      9300
aaccaacagt taaaccatat cgtggttctg ataaccaaaa cctctggaga aaagagtatg      9360
gatggcaagg cgattgtcaa tggcgagcag agtaaatctc gtcgtaaaat tggctacgga      9420
aaaggtgaga taatgattat ctcttttaat agtgctttat taggcactta taaggttaag      9480
actgaactcc ttgatgagtg gaaaaagtat acaaactcac tttttggtaa tgttggaatg      9540
gaagccttag cagagattga gaaggctgga acattcgaag ttgttggtaa aggccacttt      9600
acaatgttct acagaacaaa cctaaacgtt ggtgacagta ttgttggtgt cactgaagaa      9660
gaacttaaaa cattttgtga aaagattgag agagatacga aatgggaatc tggaacagtt      9720
ttaaatcaaa aataaaagca gcactggcat cactaggtat gctcactggt gttgacgtta      9780
ctcatctcat gcagaacttc aagatggatg agaaactagc taatgagatt atgaaaagca      9840
tctatgtagg tcgtggaaaa ggtggtaaaa aacaagcaca tcgaccaact ggtgcagcag      9900
caattaaacg tgcagctaaa aaagctcgta accgtaaacg taacaagaag gctaaataat      9960
catgagcaaa gtttataaca ctcgtaaatt acagattttc gtactgtgcc agtttatggc      10020
taaagagtgt aactactact attgtgggtac aggattcatt agtgataatg acggctcata      10080
tctaccattc aaagaggctg taaaactctt caatgaagag aaaagctcta agaaagatat      10140
tgaaaaggtt aagctaaacct acagcaagaa agataagaag attatctgcc tagataactt      10200
tgtgaaagtt actggagaag caaaagagtt tatggatgag agtgaaatct cattcacaag      10260
catcttgaaa gtagctcagt aaacagatac tataagggga ctgtaaaggt tcccttttta      10320
ttttggagat aatatgtatc tgtcgaatct aaaacgttct gctgcaatgt cagttctaag      10380
actcagcttc gatgaacgtc aagagttcat taactcccac caatacgacc cttctaactc      10440
aaatcacatg attctctgga atcgtgacag tactcgtgaa agagcactat tccgctatta      10500
tccacactac actgtagata acttgtatga atgttttgtt gtgaagaaca ccattgcagt      10560
tctcaataaa ctttgcagat acacaggtag tcaatccttc acattaggtc accacaagcc      10620
tgttacaaaa ggtggtgaac atcactgcgc aaactggttt atccaaacta agctgataa       10680 ccagaagcaa ggtgatagcc ttctaagcac ccctaagatg acctatgaag agcaagaaga      10740
atatatcaaa aataatatgc cagatgtgct tgacaacaac tatacagatt tggcaatatc      10800
tctcctgttg aagttcgaga cagtttatag ggcaacttac aatggctaaa gagaagtggg      10860
```

```
agattttacc actagtcagt gagggtggta acggttgtga aatgtacatg atacgaggtc   10920
atgttccaga accaattgca cttgagatgg taaacaattt tacagatggc tcctacaaag   10980
acttaggaga accaactgtc aagcaacaat gggttaaacc tgtaccagac agcacaggta   11040
actgtagtgt actttatcac gttgtagacc ctgcaaaatg caaatctgca atggcagtaa   11100
caaacgtaac ttttgattga gagagaaaac tatgaaaaca tctatccgtg ttacagttca   11160
ttcaccaact aaagggactc atgaagaaga gtttaacatc atccaattcc cttctggtga   11220
gattggtgga cacttttcac cagagtttgt tgattttact gcctatgcag catcatctat   11280
caacaatgtg attatgattg taaaaggtta tgataaagat acattgtttg ctgtggcact   11340
tgctaaagaa gcaattgatg acttagtacc tcataagttt gctatgaaga ccattatctt   11400
ttactatttg ccaaatgcac gttatgaccg tcacatgttt aaaggtgatg cagcagcttt   11460
gaaagtgttt gcacaacagg ttaatgcaat gggttttgat gcagtctgtg cagttgaccc   11520
tcacagctat gtaccagaga acctatttaa ctgcttccag agtattcctc aaaaggaaat   11580
tgcagtccac tatgcaaatg acccactggt tgattactta gtagcccag atgcaggtgc   11640 tgctaagaag attgcagaga ctgctaaaga ggtggataaa ccatatatca caatgtctaa   11700
agtacgtaac cttcagactg gtgaaattac tggtatgcga atccttgatg atgtggattt   11760
gacagataaa actgtcatga ttcttgatga tatctgtgat ggtggtcgaa ccttcataga   11820
agcagctaaa catcttcgtg aagcaggtgc aaaacgtgtg gaactctatg taacacatgg   11880
tatcttctct aaaggtgttg aaaaccttct tgacaatggt attgaccaca tctacactac   11940
aaactcttta ggggaagcta aagaccgtgg tttaacacat tatggtcaag ttactgtagc   12000
aaatttggac taggtaacag tatgaataag ggttattttg aaaaatacct aatatatgaa   12060
ccagatacag gtttattaat ttggagagta acccttttgca gtaccgctat tgctggtaat   12120
gtggctggca caaggtctaa gaagggttat atccaagtcc agataaataa gaagaggtac   12180
tatgcacata atattgcatg gattatgtct gggggtgaga taccaagtgg atatgagata   12240
gaccacatag accttgataa agctaataat aagttggaga acttaagact tagcacaaag   12300
tcacaaaatc agaggaatag aggtatacac aagaataata aaactggtgt gaagggtgta   12360 agttttgta aacaaacagg tctttacaaa gcaagagtca tgcttttacca taaagaatac   12420 ttttgtggaa gatttaaaac ggtagaagaa gcaaaagaag ctgtaattaa aaagcgaata   12480
gaacttcatg gtgagtttgc aagacataac taagagagag ataaaatatg agtaagccac   12540
tttacgcagt accagcaggt cttaatgcag atgcttacaa ggcatcacat atatatcagt   12600
atccagatgc tacacagtat cttatgttga acctgacacc acgtagtgat aaatggttta   12660
acagcccttt agcaattgac ggtgtagtgg cttttggtat tcaacgtttt gttaaagatt   12720
acctgataga ccactggaac gccaccttct ttgaacgtga caaaaaagaa gcaattgacg   12780
aaatcttaga agtcatgaac ggtgttctgg gtaaagatgc tattggtcga gaacattggg   12840
aagcactcca tgacttaggt tatctaccag ttgaagtata cgctgtagaa gaaggcacag   12900
ttgttcctat gcgtgtacca atgattgtct tccagaatac tgtttcaggt ttccattggg   12960
tagctgggta tctggaagat gctttctctg ctgagatttg gaaggcttgt accattgcaa   13020
ctattgcatt gcactacaaa cgtatctgta agaagtgggc tgaccttact gcgacaacg   13080 acttacattt accttatcag tgtcatgact ttgctatgcg tggtatgtcc ggctttactg   13140
atgacgcatt taacgctgta ggccacttaa ccagctttaa aggaactgat agcttcccta   13200
```

```
ctgtgtatac ggctaaacga atctatggac agtcctaccc aatctctgat attggcagct    13260
ctgtaccagc cactgaacac tctgtgatgt gtgcaaacat tgcttgggaa ggtggtaatg    13320
agttgattga agaagaaaga cgctttaaag gtgagttaca aaccttccgt cgtttcttaa    13380
cagaaactta cccaaccggt attgcaagtg ttgtttcaga cacttataac ttctggagaa    13440
ctgtatcaga atcttaccca gcacttcgca aagagattat ggaacgtgat ggtaagctgg    13500
taattcgccc tgactccgga gaccctgtac atattgtcac aggttataaa gcaatccact    13560
tagagtgtgc taagaaggct tattatgaac accttagtaa gctagaggcg agtgatacaa    13620
tgctgaactc tgtcctgaac atgaagcttg aaaacattag ctatggtatt gctggatggc    13680
tactgtcaga aggctatgaa atggttgttg acagagaaga ctttgaagct gctgatacgg    13740
tgatgttgaa agacgcttat atggttggtt ctgcaaacgt tgtaacacgc cctgtagctg    13800
agattgatgg agctattaag acactgtaca acatatttgg gggaactatt aactctaaag    13860
ggtttaaggt actggatgag catatcggtc ttatctatgg cgactctatc acactggaac    13920
gtgcaaacga atcctgaag cgtctgtatg aaatgggttt tgcaagctct aacgtagtgt    13980
ttggtgtagg ttcttacact taccagtaca tgacccgtga caccttttgca tttgctgtca    14040 aagcaactct tgcaagcatt ggtggtaaag agattatgct tgcaaaagac cctaaaacag    14100
atagtggtgt taagaagtct gcttttggtg gtgtagcacc tatgtgggat ggtgataagc    14160
tgaaagctgt agatggctat ggattccaga gttttgcaga cgtacttgac cacccagctt    14220
gtgctttacg tttagtcttt agcgactctg agcagtttgg ttacacaact cttggagata    14280
ttcgaaataa tattgacaag cagctttaaa agtatatgat aagaggctcc tacgggagcc    14340 ttttaattt ctggagaaga ttatgaaaat caaagagatg aacatcaaca ttgtcttaga    14400
agaacgttgg gagaacatca agaagctga aaatggtcat aagttcctca acaaaatctt    14460
agtagcagcc aaagaagaac tgactggcaa ggttgcagcg gcaatcacaa taaaggtctg    14520
tgtaaaaggt cttcccgaca atcaccaatt tgcacttgac gagttcaaag aaagcttcta    14580
caatccaaac aaacagatgc ttgaaagtaa ctttgcagta tcgacaagta tcgtccatga    14640
cagaagcttt atcctttaca agaatatgag aggtgagtca tgcaagcata ttggatagaa    14700
attttactgt cactaggtag tgtatcagta tttgtttacc ttctttgcaa gtactatgca    14760
gaacacaaaa aatgtgactt ctgtaatgga gagggttata caagagcagg ttgctgccct    14820
atgtgtggtg gttctggtaa aatgtttaat aagtaattta acagtaaact aagaggaaag    14880
tattatgcgc atggtaaacg accacgcaga agtgattaag agttcaactt ctttagagac    14940
gtctcaagca cagattacaa tgacacctga aatgttcagc cttttgagtt ctggtgtata    15000
tacctttaaa gaaagggcag ttattcgtga actctcatgt aacgcagtag atgctcagaa    15060
agaagctgga aaagagaaca tcccgttcca tgtgcattta cctactcgtt ttgagcctta    15120
ctttgaagtt cgtgattttg gaactggatt gactcatgat aaagttatga gtttgtatct    15180
aaattacggg gcttctacga agaatgactc taatgactac attggtgcaa tgggtatcgg    15240
ctcaaaatcc ccatttgcaa ttgctcagtc gttcacagta tctagctatg ttgatggtgt    15300
tgttaataag tactctgttt accttgagaa tggtatccct caagtaacta agctgactac    15360
caacccaaca aaagagccta tggtttagc tgtacgtgta gcagttgctg accaccgtat    15420
ttcaaagttc tttgaagaag ctggtcacgt atactcatac tttgctgtaa aaccggaaag    15480
taacattgag tatgacgatg tattatcaga tatgaatgtc attgcccgtg aagaaggtgt    15540
ttatgatgcc atgattcata gcaaagctg gcgttctagt ggtaacagga cagcgtttaa    15600
```

```
tgtagtgatg ggtaatattg cctaccctgt taacatggaa gcattacttg gtgatgattt   15660
cttcaaagtc ttgccagaat ttttccgtag gagcgtagac cttgtaaaca tatacatgcc   15720
tattggctca gttgctattg cagcttctcg tgaagcattg cagatgaacg acacgacaaa   15780
aaatgttatc attgaggcta ctaaaaagat aactgaagca attacaaagg atgttatcaa   15840
gaaagttaac agccaaccga cactcatgga tgctgcacag gcttatgctg agttacgctt   15900
gaactcacga gagatgttta atgctgtgtg tccaaagcta gagtggggag gtgttaagct   15960
tgattctctg gaagaagaat tactaaacat tcgtcgtgga attatctacg cagaagacgg   16020
ctcagtcatt tatgaacgtg acggtaaagg taatattaag gttgatagga acggaaacaa   16080
cattcctaaa gtagattatc tttatgaccc agttgcttat gtcaagttca actctttaga   16140
gagtaagatt cgtgcaacat cactttctta cactcaagag gcaagtatgt tcaatatctt   16200
tggcgcaatg cgtaaaagcc aaattgaaca gttttttgttt gttataaatg accgtcgcaa   16260
taaaaacggt actgagaaga ctgtaggacg aaatcaaatc ttgcgtggtg catgtcgaga   16320
ctatgcaagt gagtctagtc tgtttcacag atacaacggt attgtcttcg tattctctaa   16380
tgagaaagag ttagacgacc taatcaatct acacaaactt gataaaagct tgttaaagat   16440
tgtgaagatg tctgataagg aacatcatta tcagcgtaaa gaagctgtaa gaggtgttgt   16500
aaaactctgg aaagctgttc cagcagaagg tgtagcttca tacaaagagg tgtcagaaga   16560
cttagatacg attgaagagc ctcagcttta tattaaggca gtaggcgaca cagttgatag   16620
tgaatgcttt tgctcatctc cagaagatgt agctaagtca gttgccaatg tcattggaaa   16680
gacagtctat gttttccgaa aagcaaattg gaaaaagata ccagaagact ggattgaagt   16740
agatgagaag ctcttgaacg acagcttaac tgatgttcac tggattaacc ataacaggta   16800
tatgacacgt atctatatga atggtgtcct tgaccttaca agcagttgga ttattgccag   16860
aaactttacg ttcaataaca ggaagatttc tcgtggttat tgctattcac gagatacaaa   16920
caaaactatc ttcctagaag gtaatgaaga tgctgttgag gcaatcttcg gtaaaatcca   16980
atacgttgct gcaccgtttg catacactta cactgttagc aggttgcaaa ctttgaaaga   17040
atgtcttgac aacgatacaa agctgtacaa gaaaatcaaa aaagctggtg accatatggt   17100
tattaaggtg acaaactacc tttcaaaaag aaaacaagaa aacttcttgc tttctcatct   17160
agattggaat aaagtgtcac ccatcgaagt gagcaagttc ttaggctttg atgtgaagtg   17220
tgttccagaa gggactacaa tttacgatta aagtgtttga caaggggctt gaagcccct   17280 tagataacc tcacaaaatg atttattaac taacaagaga gagtaacaag atgactacta   17340
aaactaaagc acagattgac gcagaaattt acaaactggt taagaaggc aagctgacta   17400 aaacagctat tgcacagaag ttcaatactt caacccgttc agttggtcgt gctgtagagc   17460
gtcatgaagc aaccttaaag ggtaagaaaa aggtagcttc tacaccagct acgaagactt   17520
tgaagcaagt tgctaagtca gttaaaaaga aagctggcaa accagttgaa aaggttgtta   17580
aagaggctgt acaaaaggct ccggtaaata aactacacga agctatgcag aatggtgaca   17640
agattgaata catgattact ggtgactctg taattatgac ttacggttca gaatctgaaa   17700
ttgttgagtc tactcatccg aactatcaag agattgtagt tcatgttgtg aaaggtgagt   17760
tcaagaaagc tttcgaactg atgaacattc gtaaatctat cgaaaacttc actcagggag   17820
ctatcacaat caaaggtgac aagctattct acgtgctgt tgagatgcgt tctactctgg   17880
ttgaccgtat ccttcacatg atgaagaccg gtgataaagg ttttgaacga cttgtaatgt   17940
```

```
tcttcgaaaa actgatggaa aacccatcta aagattctgt agaacaactt tggggatttg    18000
tatctcacct tgatgttgaa attgatgaag aaggctacat cattggttgg aagaaagtct    18060
ctacttgtga aggcaagctg gttgactctc acacctacaa agtacctaat gatttgggta    18120
acattgtaga aatgccacgt tggatggttg ataacaaccg taacgtgact tgctctcagg    18180
gtcttcatgt tggtgcttgg gactatgtcc gttgcttctc aggtgataca atcctgaagg    18240
ttcgtgtcca tccacgagat gttgtatctg ttccgactga ttacaacgat atgaagatgc    18300
gttcatcccg ttatgaagtt gcagcaatcg ttgataatca acgtaaagtg ctgaaagcat    18360
gggatggtaa gactgaggct ttgcatgtca tcgttggcac tgctggcgaa ctcatctctc    18420
aacgtaagcg tgaaatctaa taagtaattt cttaaaaggc tgcttcggcg cctttttta    18480
tttgtatttt gtgcagagtg ctgtataatt gttgtcacga taaactaaac aggagaacca    18540
atgaagaagt tgattctagg tttgtgctta atgtttacag cacacttatc ttatgcagtt    18600
gactgcccag agctatcaat tagtcaaaaa gtaaacatgt taaaagctta ccagtatggt    18660
gagaataata tgggtaaagg atggggcatc actctagctg ctatagcctt acaagagtca    18720
gagttaggta tgaatatgga gaataaaaag acccatgact atggtatctt ccagaatcac    18780
ttgaagactg ttgtaaagcg taacaaaatc agtcctaatg tggctaaaaa gaaactctta    18840
aaagacttcg actatgctgc aaaggaaaca cacaaagagc ttgagttttg gacgaaggta    18900
catggtcaac caaagtcaaa gagactttta caaaagtttt tagcgtcata taatgctggg    18960
tattcgtaca aaattcctaa agctaagaaa tactctcaag atgtctataa caatatgaaa    19020
gttatcgcgc aatgtgaatt tgcaacaaac atttctaagg taaatcatga aaaaatcaag    19080
aaagtctgat gaagtcctgt gccatgctta cgacttgcac cctcatgagt taggtcttga    19140
ttcctgtgta tggactccag aacagtgcag ggattttgaa gatactgcaa gagaagttgt    19200
atgttcactt gaagagttcc atacaccaga gccaatcgtg aacgttatgg acaaagagac    19260
tggacaatct ataggtgtaa gacgtgatag cctagtcata gttaacaaag accttgtaga    19320
aaaaggtaac ctcatcttag cagatattga tggagttctt acaaattta atcacgaaga    19380
gtactcaaca gagttgactg acgggtcatt ttcacagtac actaatcttc ttgactctgt    19440
aagagcaaaa ccaacatata ttttcaatat cattgatgca attgctaatc atgctgctat    19500
cggactcttg acagcaagag gtgaaactca gagaatacct actgagatgt tcttgaggca    19560
caatatagaa catgattaca tgcttttat gcgaggtttt ggaactaact ctctaagtgc    19620
agaaagttta aaagtgagga tgattcagtc ttgcattctc ccttacttta atatagtatg    19680
ttttatagaa gatacagaga agaatgttca gaaggtaaac agaatccttc cacacattaa    19740
aaccatgtta gttaaacatt gagagaaaac ttatgaacaa tatcattacg gtagcactgg    19800
acgttacgga aaacaaatct gaagtagttc gtaacattat caaaagcaac tttgagggta    19860
aaatcttccg tgctgtcaat gtaaaagcag acgggaacat ccgggagtat cgtgctcttc    19920
tgaatgttaa gaaacatgtc aaaggtgctg gttcaacgac tgcacacaaa gaaacctga    19980
tgactatcta tgatatgggt atggcttcag agttaggtgc tgaaggtatc gttaaagaag    20040
gtgctccgta tcgctctttc aatctggaaa ctgctcttat gctttccttt acaagtggtt    20100
ctaaaacaac tacttatctc tttactgatg ctgcaacggt atctgctatt aaggatagca    20160
ctgtcaaagc tggggtagct gctgctgcaa aagcttcttc gatggctgca aatgtccttg    20220
ctaaagtcct cagttaaggt taagatacag gctcctcgg gagcctttt catttcagga    20280
gattgttaaa tgacatttaa agagttctgt caagctactt tcataattgt tttcttagtt    20340
```

```
ggggcaggtg tctggggagg atactcctac agagactacc aagttgctga agctgagcta    20400
aacaatgaga aactgataag tgtcgctaaa gatgcttatc aggaaggttt agtcacactc    20460
agcaccaatt acaaaaatga tttgaaagac gtgcttgcta agaataagca tacaaaagag    20520
gtactaacat atgaaaaaac taagccagag ttttataatg tttgtgttac tgataattat    20580
gtcagggtgt tcaacgaaca aagtgaacag tacattcaaa aactcccaag taagtgagag    20640
tgacaagtac actcaagaag aatcaagatt cactgtcaaa gcaacactg gtagtgatgt     20700 ggcagcagcc cttgagtttt atcgtgatgg ttttaccag tgcacaatca aagctaataa     20760
ccttattgat atgatttat taggaaacaa acagcaatga cagagaatga agacactttc     20820
tatgtagaag ggtacttact gctaccacga ccaaaagaaa cttatatgcg tgttgatttc    20880
tcaccaacca ttatggacaa cgtgatgtgt catatcttta tgcaaggtgt cacagcacaa    20940
cttaagcatg ttggtaaaga gtgcaaaata aaggttgaca ctcatccaga aatcaaagag    21000
aatcactaca catggttctt accagactct aaagaaatct tagcagttct taaaacgagg    21060
aagtaactat gcagattaat ggaagagact ttgtagcagt ttactacgag aaagataaag    21120
aagttggcgt agcacaagta tcttatggta atggtaagtg gttgtatggg acaatcgcag    21180
tagttgggac aagaagtgat acaaaaactt ttaaagattg tgttgacctt cttgaagaat    21240
ccatccacaa tcattggtgt ctgatatgga tgactgacaa cgaagtgata gaacgcttca    21300
aaaagattgg tatcaacatt gatagtattg agcatgttga tttatatgaa ctaactgaga    21360
aggtaaacta tgaaagtaat actagccaga gataaaaaga cacggaaaat tatccggtca    21420
gcagtatcca ttggaagaaa tgaagtgatt ccttttacag caaatgatgt gataatctac    21480
aggaaaaaat tagcattcag ttattgctta cgtggcttta tctcccaacc attggaagac    21540
tttaaaagtc gttgtggtaa aggtatcatc attcaagagg caattatcaa tggctgactt    21600
ctgcaaagac tgttctatcg aaatgttcgg acgtgataca ggtgacttaa aaggtctcat    21660
cactgaagat gactttaaag ctggttatgc aatgccagta atctgtgaag gctgtgggtg    21720
tatctgggta gaccacgaag ggcaacgtgt aaaaccttca gaagataaag aatcttggga    21780
gagatgttaa atgggtattg taaaaataat caatggtgat atctttgccg catttgataa    21840
aggtaagttt gacatcatcg gtcatggttg taactgtatg aatttaatgg gtgcaggtat    21900
cgctgacaag atttctaaac tttacccaaa agcatgtgag accgatacag aagtttatct    21960
gtatgcaggt ggcataggcc acaaaccttg tgaaaattta ctagggaatt tctctgtagc    22020
acgtttagaa caaggccgta tagctaacct ttacactcag cttaagactg gtaaagatgc    22080
ccgatacagt gctttagaat catctttgaa acaacttaac agatactgtg aagtcaatca    22140
gttgaagaaa gttgggttac ctatgattgg tgcaggtatc ggtggactag actctcaagc    22200
cgtcacagtc atcattaatc aggtgatgaa gagtgtagat gtgtatctgt atgtctatga    22260
aggagagatg taccacaagt tacgctcagg ttggaagaac tactgtgaac cagaatactt    22320
tgcaggtgta gtagtgttca ctaatgatgc agttaccctc ttcagacgaa gaaaaggcaa    22380
gatacatcaa agtaaccctc cggttgaaaa gatgtctcta agtaacgctc tagttaccca    22440
cctgtcgaag agcaatcaca gaattgcagt aacatttggc agtgatgcag atacatatat    22500
ctatgcaaga actgatgagg atgttgagga atttctctct tcaccggaag taaccttctt    22560
agacgcaaag aactaagaaa ctctgtagaa tattcacaat aggttaagcc tttcttatct    22620
ggtaaatttt tcaggtaagg agggcttttt catttcagga ttgtgcaggt agagttctgg    22680
```

```
acagaaatct gtagagaaaa ttttgaactc caaagagaaa attcattttc aaactgtgca   22740
gataatctcc aaagagcttt tttattttca aaacgtgcag agaaaaatca ggtcgggcaa   22800
gaaaaatcat tttagaattg tgcaggtagg tgggtgtagg tggggatgtc gctatttctc   22860
acaaggctac cacatctgaa aagaaaagtc aacagaaaaa tttgtagcgg attgaaaaat   22920
aattcttgat tgtagttctg ttttgtggta ttcgcgtgcg cccgtttcat tacattttgc   22980
caaaaatatt tttaaaattt ttcttgactc tttgaacggg tttttatagt atttgcatca   23040
gacgggcaaa caagctcaac aaccttaaac taggagattc aaaaatggca tatcgtgcac   23100
ctaaattcat caacaaagac aactttcgca acgcactgga gaagtcactt gatgaaaatt   23160
ttaaaggcaa cattatcgtt gttcacgcat tcaattttaa gtatgatgta aacgggaata   23220
gaatcaacca ttacacggca accatgttag atggtacgct atcaagtgaa aaagctgtac   23280
tgaatgcact tgctggacgc ggtaaaaacc tgataaaatg tgataagaga cgttatcagg   23340
gtggcgcata tggttatgat gatgctgttt accatcttga aaatatgggc tatgcagtag   23400
aaaaagctgg ggtatcacaa atcatcggga gtgatggtta tgtgacaatt ttcaaaatta   23460
actaataaag tacttacaa ggggcttata gttcgataga gtaagcccca gataaagagc   23520
tttaccacta aatcctaaat tggagaactt aaaaatggct attatcaaaa acgttgtaat   23580
tactgcaaag actcgtgatg acgctcgcgt tatggctaaa aagttaggcg ggaaagtggt   23640
tgacaatggg aaacaatctg ctgtaaggtg gggcgtgaaa gctgataagc aactaacctt   23700
aaaacgcagt tcaaacaacc tttttaaagg tgtaaaatca ctcggtaaag tgaacgtttt   23760
taccaaaaaa ggctataaaa tgcacttatc attaactggc aatttaatct gataaagtac   23820
tttacaaggg gcttaaaagc tgatatctta atccccagat aaagagcttt accactaaat   23880
caagtcctta aactaggaga ttcaaaaatg aaaactgtag acgctacctt tgaagttgta   23940
aaagaaaaat tttccatcat ttatgaggct gttaacactt atcaaccatc ttatgtaatg   24000
gaagatagct gggaatttac tgataaacat catggcgggg taactgttaa gaatcctaac   24060
tatgaacgca atggatacaa atatgctatt cctttaaact atagtttaag ttgccttgct   24120
agtgactatg caaacaagg ccgtgaaaat ccatcattag aagcttatgc atcaatgcaa   24180
aaatctttaa agagggattt agaggcttca gaatactacc ttgctgcaaa agttgtagat   24240
gcaaacggta acacgttttt agatagtttt agtattggat atgtgtttga ttggtcttac   24300
ttggacggcg atgatttaga tgacaggcta aaagaggaag tgaacaacgc agacgcagaa   24360
tctgaagtat tagaacgctt agaagcctta aaagattcag tgatgaatat ctttaaaaat   24420
taaattaaga gggaacatca tgttaatgat gggtatcact gcaatcatcg ccattatagc   24480
actttacaag gcttacagcg cctacaatct ggcaagtgag gcaattactc aacaggttaa   24540
taataacctt gtagtgagct ttctggagcg tttaagtgat gaacaactta acgcttaga   24600
aatgagcttc agatttcaat caaaaactta tcaaatcagc gacatttca agaggatttt   24660
tcagcttgtc gatgattata acgccctgat aaatgcttta aatatcagtg acttaaaaga   24720
ctattacgct gtaattgttc aggagttgag caaacgaaaa caaaacagtt gacactgatt   24780
tttagatata ttaaattaca catcaacggg gagggaatga ccttcccac taagtaaagt    24840
ccttaaacta ggagattcaa aaatgtatac tactaacaat ggccgtactc taaatgtcac   24900
tctacgccac tatgtagacg gcgtgatgaa ctttgaggat ttacaagcgg aacaacatat   24960
tttggattgg caacttgctg gacttcaaaa aactgctacc ggatatggga aaaagatacc   25020
aaccagctgg aaagtatact acaaaggccg tttgcgcaga atttaccaag atgtgtgcag   25080
```

```
caatagcgca tcaagttaca tcatggtaaa aggcaaaaag ctgcatttag tgtaaagtac    25140
tttacaaggg gcttatagtt cgataaagta agcccccaga taaagagctt taccgctaaa    25200
tcctaaattg gagaacttaa aaatggctat taataaccgt gaattcttaa tcttaaaagc    25260
acgtttgacc gtcaaccgga ttaatgttat cacgtcatca gcgccagacg aaacactgca    25320
aaacattatc gggaagattc aaagtgttat cttagacgtt gaaagcgtaa aaaactcact    25380
gattgacgtt gcagcgggta tcacgctaga cggcgcacaa tatgaaatgg ctgacatgtt    25440
aggcaaatct aaggtaatga atagagagct ggatttgaaa atgtttcgtt ttgctgttaa    25500
agtatggcta tccgtcgagt atggcgcaaa ttttgcaatc gctgactttt tcgcaacatg    25560
gttacaacgt aatttaacaa atcacgattt tcgtgatatc tgcgacgtaa tttattcaga    25620
actttaaaaa attcctcttg atttggttt  ttaaaacaag taaattacta atcaacgggg    25680
agggaatgac cttccccact aagtaaagtc cttaaactag gagattctag aatggctatc    25740
attaacggct taaacattga aactactcac atcaaagata tcaaagttgg cgatatagtc    25800
ctttttcacg gcgtagaaaa aactgttact tcaaaggata tcaaagagga ctctttcatg    25860
ggccggtctc tcttcggtga ttcttattgc ttaggttatc gcgcagtttt aaaagttgtc    25920
aaaaataatc gttaaagtac tttacaaggg ggcttatagt ttgataaagt aagccccaga    25980
taaagagctt taccgctaaa tccttaaact aggagattca aaatgaaat  gctttcacgg    26040 tactactcaa gaaaacttta tcaacctgat taataacggt gataagccat caggtgcatg    26100
gaattgttcg gatatggacg gcaattttta tgtttatcca gaaaataaaa tctatggcga    26160
cgatgcggaa gagataaaat cggaaggaat tcaacaagcg ctaggaaatg ccactatatc    26220
agcggccttt caaatgaaaa ctcaaaacat tgttatctta gaacttgata ttccagaaaa    26280
tgagttaaac gatgatttct cttgcgataa tatgtctagc gtggcaagtt ttacagagta    26340
ttttgatata aactggatta aaaaagttta catcactgaa tttaatgcta tgttttcgcc    26400
tttttgtctt ccttcactag ataacccgaa tttaaactat attgaggagc ctctagaact    26460
tctcgctaaa agtatccaac aatcagacag tattcaggtt ttttgtgaca tcatggacac    26520
actgacagga aacattacag aaagagattt aaagagcttt ttctaataat ctatacaatc    26580
accttataaa cactatttag cccctataag gggcttttag ggggcttaaa tcatgcttat    26640
aaccgtttat cttatccttt ctatttgtaa tgggtattca tgcaatttta aagggcttga    26700
ggagtttaca ggaagtaaag aaaatgctat acaggtttgt cagatagcaa gacaagacta    26760
ccccgccagt gatgatatac aatgttactt taagacagaa gacaaggacg gcgtttattt    26820
tgatagtgtt gacggccaat atgagattat cattgaaaaa gactagacaa gcctgataaa    26880
agtctgtaaa ttgtcaatca cgggaggga  taacctcccc actaagtaaa gtccttaaac    26940
taggagattc aaaaatggct tatgtaaccg taattaccga caaagctggc gcatcttggt    27000
caactcaagt aagtgataag atgacaccta tgcagtgcct aaaatacttt gaacaatgga    27060
acaaaggcga gggtacaagc acctttcatg tgatgcgtat cgttcacact gacaaggaag    27120
ggaataaaac ggccttgaat agtgaatact acgcaaccag attcgaaacg agaagtaaaa    27180
taatgaagct attacgtgaa tccggttatt ctcatatcgc cgctttaatc tgggatgatt    27240
tgctcaaagg ccaaaagatg aactatgtaa aacctgaaaa aatattcatc agttaatcaa    27300
taacttacaa aaaacttta  aaaaagtgtt gacaatccct cttgacattg gtaactttgt    27360
tcgagggggt ttatctaaaa gggattcact taaaagattc tttatagata agcttaaaaa    27420
```

```
attgcttgca aaggtaagtc aaaacaagta aattactaat caacgggagg ggataacctt   27480 cccactaag taaagccctt aaactaggag attcaaagat gaacaagttc aaagctatca   27540
attacattcg ttcaagtgct gtaatgtcaa acctgttaa agacacttac gaatttcgct    27600
gtaatggtgt acactttgca accatcacca agtcagaaaa tggggcttac tacgttcacc   27660
gtcgtaatgt tgcaaccgtt gtagtctctc actttatgca agctgtcgcg gaacttctcc   27720
cgatgttttt agggctttac ttagatgagt gtaaaaacgt tcacaaacac gttaaaaacc   27780
ttttaaacag ttatagaatg cttatgagc gttctatcaa gtccttaaac aagttttata    27840
aagcccctgt aaacactgtt tcaatggcct atgctgcaaa tggtgagatg gtaaacttat   27900
ccaatgtgga agaaatcgaa ctgcataacc agcggcctga aggttactct aaaaccatcg   27960
gtgaaggctt atctttcaat atcaagaatt tagaaaaaac tttaaaagat attgataaag   28020
atatcgacga gacaatcaaa aatctgtaaa ttgtcaatca acggggctaa aatagcccca   28080
gataccttca aagctccttt tcataggggc tttttacgt cttatcaaat ccctttccct    28140
ttccagaatc ttacccattg attcgataga atctatctca taccttaaaa agcaataact   28200
ctatatctta ctctatagcc ttttattaaa tcaacttaaa tataagccca taacccgaga   28260
gggaagggca accatttaaa cgctctataa agctctataa cagccttatt aacctgactt   28320
aagggattgc attaactcac cattaaaagc ccttttataaa gctttataga ggcttaaaag  28380
agccttaaaa gaatcttata agggtgtaag ctttatcatc ttgttagcta tcttgtgaat   28440
aactaaaaag ggcttgataa tacttaaaag gtatgctatg gaaagcttaa aagtggctat   28500
aaagttacgt aaaagttgct taaaagttac gtaaatgcta gccccccttaa cattttctta  28560 acaatttctt aacaaaccct acatagttat gcttgttagc aacttgttag caccttgtta   28620
aatctctgtt acaaccatgt aaaagccttg taagaacatt tgacataacc tttaaagctc   28680
ctgtaaagcc ttataaagag ctttctacat agttggggtg taattactag aaagagacta   28740
aaaagagctt ataaggagct ataaagggct tttaagaggg ctatttaaag agtcactaag   28800
agggaaaggg aacgataaga aaagagatag tgaccatgtt aacagcttgt taaaaagatt   28860
aaacacttgt tagaagcttg ttaattatct taacaaaata actcttttaaa attaacttgt   28920 tagctcttgt tagtcatctg ttaagcatct gtaaagacca tgtagcaact gttaagaaac   28980
tgttaccctc ttggtaaaac tgttaaggaa ctgttaagac ctctgaagag atgttaagaa   29040
gatgtaataa ctgttaagag attgttaatg atatttaaa attctgcaaa ggggatgtta    29100
cagggatgtt aagggctacc aagcagatat acatcatgag gtagattcta ccgaatcaac   29160
tctacagata tttttcagtt ccttcaaaga ccctaaaaaa tgacttgata gtcctatttt   29220
ataaaaaatt taaaattctg aataattacc tatacagtct tttaaaaata caggcataaa   29280
caggcttata agataccttg ttaataccgt gttagacctt gtgagataag gtctgtaaag   29340
atattcctgt taagtttgtt aaaacagtct atatagaggc ttagtaatac ctagtgaaca   29400
cctatagagg gtaacatagc taacctagag attaagaggt gtataggagc ttctaagagg   29460
gtatagagag atggttaagg tgactgtata ggttgttaag aaggcttgtt agagggctat   29520
ttaaagggat gtttagaaga gttatacaga tagctattaa gaccactaga tagatactaa   29580
gatactatat agtactatat aactaatata gagagtaagc ttaagcagat gttaagaagg   29640
tatagatatt tttattcaca tatcatggtg acccagaggt tggaacaacc gataaaattt   29700
tataaaaaat aaaaagcccc ataaaagggg ctatgtagat attttaaaga actgtttcaa   29760
ccacagtttc taaagatgac ttagttgtct gataaaaatg agtaaaccct gtatcgttat   29820
```

```
cacgtatctg caacatgatg ctttctcctt taatcgggaa ggactctatc acacaatgga    29880
aaccattgaa tacagaagac ccactcatga ggttataaat atgaccaata gaaatatatt    29940
cctctcgatt agagagctta atacatatac ctttgtgtgg tctcttaggg tctatatcct    30000
ccatgacttc cataggqtga ccgccaagag atgtcatagt aaccttctta cggttctcct    30060
gtttaagatg cattttaact ttatctaaag tttcttcata gaacggataa gattcatcta    30120
caaagacacc cttaagaggt ggcaaacaat tttcaacctc tctgtgatgt cgtagagaga    30180
atacaatctg gttaagtgta tctctagttt cttcagacaa atattcatta atgtcttcta    30240
aactcaagac taaatactgt cgttccgagg tagtttcttt tttcatagct attaagtcct    30300
taaaacactt atcagtaatc tttgaccatt ctacagagtt aaccttctta ttacgaaggt    30360
gaaccacatc tctcaagttc ttccaattca tcttgtgatg gtgtcccata agactcttca    30420
tcgtataact tggtaatctg gtactgcaaa cttattgtca ttgtttttaa tgaggtcttc    30480
ttctgaaact aagaatgtaa gcccacataa gtgtgtatag ttactatcgt actcaaatat    30540
tttaagtaag tatttaccat cgtgataaac agattctact acacctttg caacaacctt     30600 tccagtcttg aaatctttaa gagggtatac attaccaact ttaggaactg ttttcatctc    30660
aggttctttt agtttctcac caacttctac atcacctagt aagtgagaac tttcaaaagc    30720
tacatattgc atataagcct ctgagcattc ccagataaag caatgtacaa gagccttagc    30780
agcatgtctt gaacaattca acttatcaca aatctctttg tacatttcat ctttagttga    30840
gttgtcaagc attgcttttt gaacaacttc tttaatcttc atttcgctac cttctaagtt    30900
tctacaaagg ggctatcaag tacccctca agttattact cagactttc agttttcttt      30960 tcagatttct tgctagtctt cttctcagct ttctgttcag gctccttctc agaagttgcc    31020
ttgataacca tatcaagaag ttctgatagg tcactcttca gcaaagtaac aggctgctca    31080
ttgtagaagt ttttgtcaag ataaactttg aactcttcaa tagaagggaa tccaaaaatt    31140
ggtacaggtg tcttaatcat tacttagttt ctccataggc atcttttaag attgccttgt    31200
taatcatttc agcgattgca aaacgaacac atacagctat aattgtaggt tgcattcttt    31260
acttacctct tcaagtttaa cctcagaatc cttaagacgt ttcttatgaa ctctgaatct    31320
cattagtgcg atgatgatac caactaaagg gacaacatac aagtaccaaa catcatatac    31380
ctttgcggta atctgtgtaa tggttaagtc ttgagctatg taactaattg ctgatactgc    31440
cagtaatgtt gctaggaaaa atgccagtac cattaccgta cttaaacaac ctctggcatg    31500
gtgttcattc ttaatgcact tattcttttc gtcaacaact ctgttgtagt catttgtaaa    31560
gtctctgtag aaagctttca ggtattcttt attgtagcct tcaaagcaac ctgtaccgta    31620
ccaataatca ccaccaaaat gagctatgat accagtatcc ccatttggtt tagttactct    31680
caaagaggtg tgatgacgag tatcctgata atctatctta tatctttctt cgtaaatcat    31740
tttccaaccc ctctcaatcg tttgttccat tcaaggtcaa caagtctttg caggactttc    31800
cctctaggtg ttacaccttt taaatctgca tcgtagcaac ggtaaaagtc accttcagcg    31860
tgtttaccat agcatttttct gatattctga cttctacgat attgttctaa tagagacagt    31920
ctgtagtaat cttcaactgt agttagtttt ttcattcttt caccacgcat ccttttaaga    31980
aaccaaaaag ggaactacct ctcgatagtc cccatcatag ttaacattgt atattcggtc    32040
aagagtattt tttaggcagt aatgcgctac gcttgttact ctcttcactc aatagtgcaa    32100
tgaaatcatc acttttacct ttccacgggc tgaatgaagg aatatgttca cgaatagcct    32160
```

```
caataaccgt cttaagtgct gtgttcttca tccaccaatc agaatctgct gatgctacaa   32220
catagtatcc accttcatca gtcagaattg gctctgagat acatggtgaa atcagagtgg   32280
tgacgattga gccattattc atgtagtatg tgcgcttcat aaccttttca agaagcttgt   32340
gaaggtcacc aaacagtgtt acaagctctt tatggtcaat gtcttttcg agatttgctc    32400 gatacttcaa aagtgcagca tcaacttctc tgtcattaaa cttgaagtac tggacttcct   32460
caacaagaca aacactgatg ttgttaacat tcatagtcaa cttgcagact tttgcaggag   32520
aattgatatt tggttgaaaa agtgcaatac acccttcaat gttccaaaa tgttgtacca    32580 gtgttacttg tggagtgata ttctgttgct cttcggacat tacagtttcc tcattaaata   32640 cttttaagt tgtgtgttag gtttctcaaa aacttctata aagatatct tgacagattc     32700 accacgcata cctgtatgtt tgaatatata gtactctaac atccctatat actttgctgg   32760
taagtcatgc ttgacataca ccgttacaga atcttcaaac tcaacgacct ttgtaccatc   32820
tttgtagtta aactctttag ggtggttgta gttgtctatg tcgtacatta aaaagagtct   32880
tttccgttgc atatcaagct tattggttaa agactctttg atatctgaga agttttgta   32940 cactgtgaca tggagcttac tcatcattaa actctctgac gaagaaatag ttgactttgt   33000
tattacctac cataaggtca aagcaggtat tttcaaaagg tttgttgtag gcatcatatg   33060
aaacatatgg gtcagctact tgcttagtgc ttaacttctt acttgatggt tttaagaggc   33120
caccatacag tttcttgata gcctcttcta caacagacca gatgatttcg tcagtaattt   33180
cttcgtacag gtcaagttca cgctctagtg agaagtcaca aatagggaaa ataacctgta   33240
ctttactcat taacgaataa cctgtgttac ctgaatagct tcagttactg acaaatcacc   33300
aaccgtttct tctttgacga aggtgaaggt cagttcaata ggctcttgct cttcttgctc   33360
aacaggaaca ccattaagct catcaaagat tgattgagtt gtccagtctt ctccaccatc   33420
tgggtagtgg atggcataaa gaggaaactc taaattatac caagcaaaaa cagggcaacc   33480
atctacatca tctcggcatc tgtggagata tgtgttttgta ccttcaaaat gcaaatggag  33540
attaccattc ttctcaaaga gaatagcatc ttgcaggtct aattcctcat tttcgctgta   33600
acggctgaca tcaactttaa cgtgaatatg actgttatta ttcataaaaa cctctctccg   33660
cttgttcgat tttcgctttt agaacttcac accgttcaat gtgatatctg gcttcatgtt   33720
catgtgtcgc caaagttctt tcaagaatgg ttttatagta acctgcaagc tgctctcttg   33780
tcaatgggtt ctctgaaata atatcgagac cactttcacc cagagtatta aactgcccat   33840
gttcatttac atgataagtc tcaaacttga ataaaccgtt attagcagcc tcaataggtg   33900
agagttcaac caactcaacg gtgaacattg tatgcaccct atcaccaact gtaacaatgt   33960
tactcccaat gatgcgtaca agcgaaccat tacgagtgta cttaaaagtc ccaaagtcac   34020
tagcccaaag cttcatagtt tttctcctta gaaaataaaa aaggctcccg aaggagccta   34080
tgaagatatt actttgggta tacactgtca agataaatgt cagcttccat tctacgtctg   34140
tttttcagac cgtttgaagt ggccttctta cctttgactg taaccttgtt ccaccactgc   34200
atagcttctg cacaacctac cttattacca gcattgtggc gcttgataaa tgtagaatcc   34260
tgcatagctg tgataccgat gttgtatgtt tcacttacaa gtgcatcgaa ctcgttctga   34320
gaagttggaa ccttgatagc tttattcact gctgcaacga acttctcaac atctgcgaga   34380
agatactgtt cagcttgttc agcagtaatt ttcatacccca tcttaacagg ttttccgtca   34440
atacggattg taccataccc gattgttggg attccggcag agtcttcgta agcctctaac   34500
ttcagacctt caaagaactt aatagcttct aaacctttc ttgagagttg cattatgcct    34560
```

```
cccctgttgg gttaactgta actgttgctg cattagatgt cacagagcca cctgcaccag   34620
taactacaca ggtgtagctt cctgcgtcag tagtagttgc actttctttg gtgtaagttg   34680
cagcagttgc gtctgggatg ttttcctcac ccttcttcca ctgatagcct gttgcatcag   34740
tagcaacaac acttagtgtc aaggtgtcac cttcagtgat tcttgattg gttggctgct    34800 gagtgattgc tggtggtttg acagcagcct tcagcttagc attcaacatt gagaatggtt   34860
taactcttgc cagccattca cagtaaattg tgtcaacatc tttaccgttg atgattgcat   34920
actgtaaatc catgaagaaa tcagcagtcc tcatctgtgc accaacactg taaaggagtt   34980
catcactaaa agggacttg tagtctggtt tgtagtcaag cttcttaact tctgcgatat    35040
cagcttcagg ccaatatgag ctataggtga gtggtaaaat agcttcttga tatgttctaa   35100
aatcatatct cttaccagcc tttacatttg cgatgaagcc cttcacaaat tctttgaagt   35160
ctgggtaagt ctttgcttta atcatttctt tttagcctct aaacgtgcgt ttaatctaaa   35220
atagtcttta tgctgtggag acacatcact aacaacaata ccttcaactt tataacccctt  35280 accaattaca tactgaatat ccataagaaa cgtaccaagc ccaacaatgt ggaacattgg   35340
gtatagtaac ttatctgaat ctgggagttt aatttctggg ttataggtgg ttgttcggc    35400 agttggtgta atatcctctt caggccattt actcattctc catgtcaaag gtgttgggat   35460
aacatcatta agattgtacc tcccaccatt ctccacggaa tggatatagg attgtaggaa   35520
gcaataaaag tcttttgcac tcttagcttt cattaaatat ccttataaat agataaaggg   35580
gcattagccc ctgtttatac ttaagctttg gtcttaagta gattcttaag ttttttgaga   35640
ttcatgctct cgtcaaactt aaaaccaaat ccattgacat aatcaatgaa ctcagatttc   35700
ttactaagtg atagcgcgta actcatatca aagttattac ttgtttctgc gtctggacta   35760
gagttcacat caaatgaaat ttctgtaggc tcttgcttgc tacttctcat attatcaatt   35820
aataggcatg tatagttcgc tggatagaag tttgcactgc catcaacata cccatactta   35880
ttgttgtgaa taaggtttga aaataccctta agaaatgttt ctgagtcgtg gcatacaagt   35940
ttaaattgac tgcactctcc aagagccact aaagaataag ggctttcact atcaatgtcg   36000
tagtttggat ttgatgttgt aaccgtcaca cgcatcaagt tattggcaat agtcttctgt   36060
ttaaaagaat ttggaacata gtgaagacct ctatcacact gattaactaa ttctttcaat   36120
aggtcatttg catacggtga gttaattgat acagagccat cactattgta attaaaactt   36180
actgttaaca tttttcagtt ctcctgcggt ttataatttt gctgcaatag agaaacgaag   36240
taaactcact ggaagaaacc attaagtgtt gttcactaga ttgagccatt gccctgaaat   36300
acattccagt caaagcatcg tagtgactat tctttccaat tgaggttata tagccatgac   36360
tctttgcagt tttatataaa tctataatat ctgcgatttc taattgggaa ctacacatag   36420
ataatcctct cgtcttctgt aattttgaaa gaacaggtac agaccaattt cagaggatga   36480
atagtagagt aactctaccc ttttttgattc cttacagtga ttggtatttt tacctttctt   36540
cgggttgttt gattttctca ttaagtctcc tttgtagaac aaggcagacc tacagcttta   36600
agtaagatgg tacagtaatc catacaacaa gtcaagaact attgcaagtt aaaaaagttg   36660
ttgacaaagg acttgacaag gtgtaggctt ataaatactt agaagattac ttaaaaggtt   36720
cctctaaaaa ggctatttaa acagatatct ttctggatat ctatcttta tcttaaaagc    36780 cttttaagag gtcttataag aggcatacca atgaaaaaca gaacaaacaa aggccagttt   36840
aaaaaaggcc agtctggaaa cccatctgga agaccaaaag gctctcgtaa caaaagctca   36900
```

```
cttgtaaaag ctcaactgac cattgataat tctgctgagt tcgctgcaaa gctgtttgag   36960
gcgattgtca caagggacgc ggctaagctt gcagagttcg gtttgacgac tgacgatgta   37020
aacctgaagt caatgatgga agctggtaaa actatcatga ctcactcagc aggtgagatg   37080
aaagcaattg cagcagacac taagaaggct cctgatagtg gtggtcagtc acagacagat   37140
aacaaaccaa cgttctctgc tgtagcgact ctcaaaaaat aattttaaaa ggtgttgaca   37200
gactctacaa agttactcta aagtctgtca catcaaacaa caaatgagag aagagagtaa   37260
aatatgagcg agttatttaa acatgcgcac cttcatgcag gtcgaactga aatggtgct   37320 gtaaaccata cttcatcaat gtctgctttg gtagacttct acaaagccgc tggctcaagc   37380
cgtagtaatg tagaaatctt accagacctg ttctacaaag ctttgcgtga ggatgttgat   37440
gttgcagttc gtattttact gcatatgcga gatgtgcgag aaggtatggg tgagcgtaaa   37500
gctttccgaa ctgttttact tcaagcgatt gaagacaaag ttttagagcc tacgcaggtt   37560
cttcgcatta tggataagat tgcagaactt ggtcgttttg atgacttcaa aatcttcgta   37620
ggtactcgtt ttgagacaga tgccttcaaa catttagaag cagcattact agaccctgca   37680
acagcaggtt tagcagctaa gtggttacca cgagtaaaac cacgccacaa acagtttgta   37740
aaacgtttct gtaagtttgc aaacttaagc gagaaggagt atcgcacact gttatctgca   37800
ctgtctgata cggttgagca aaaaatctct gctaatgagt ttggtaagat tgactacagc   37860
aagattcctt cactcgctgc tgcacgttac caaaagctct ttaaccgtaa agatggaaa   37920 cgttacaaag cttacatcga gtcactctca aaaggtgagg ctaagattaa cgctggtgct   37980
gtttacccat acgatgtgat taagtctatc aagcatggta atgcagatgt tgccaatgag   38040
cagtggaaag cactaccaaa ctggatggca gaaggtgaga acatcttgtg tatgactgat   38100
gtttcaagct caatgtcttg ggtgaatctt ggttcaatca ctgcccttga tattggtgta   38160
tcacttgcat tgtatgtagc agaacgcaat actggttgct ttaagaatga gttaatggtt   38220
tactcaacaa accctcactt cattgaactg agcggtgatt tacgaaaccg tcatcgtcag   38280
gtgatgcgtc acgttgaata tggctcaact aacttacaag cagcttttga ccgtattctt   38340
gaggtaggta agagaaacaa cttgactcag aaagatatgc caagtaagat tatcatcttc   38400
tctgatatgg agttcaatca ggttgatggt gcaaatggtc gtacaaactt tgaagcaatt   38460
cagagtaagt acaaaaaagc tggatacgaa atgccacaac tagtattttg gtacttagca   38520
aaccgtaatg gtacttgcga agtatctgtt aaggataatg gtgtagcaat ggtatcaggg   38580
ttctctccag ccactttaaa agctctgctt ggtggtgaga gtttgaccc aatcagtgta   38640 atgctcaaag cagtaatgat tgaccgttac atctggtaaa aagttttaaa aagggtattg   38700
acaatgtgtt tgatacccct taagatgttc tacatagaaa cgaaatgaga cttttctaa   38760 gatactgaaa aatattttaa aaagttctt gacaatcact aaaaataat gttaaagtgg   38820 ttacatagag tttgaaaagt ttatctctgt ttagctcagc ttggtagagc gttccgtttg   38880
gggcggtaag gccggaggtt caagtcctcc aacagagacc aaattaatgt tccagtagac   38940
aaaatggtaa agtcaccact ctttcaaagt ggatatttga gggttcaaat cccttctgga   39000
acgccagttt tgcagaagaa ccaattgcag caaacttaat cttattcatc tgacacgaaa   39060
tcggacaaag aagagatttg gtctggtcat taagaattgc gggtatagag aaagggcgtc   39120
tcacatgtct cattagcatg gtatcggcag gttcgactcc tgcacccgcc tccaatttg   39180 cagaagaccg tatgcagcaa taaactactt tttgcggata aagaaaaaa cacggtctgg   39240 caatgtatta aggttaggaa gcacataagg tatgtgcggt cgcctgttaa gcgaatggca   39300
```

```
cagggttcga atccctgact aaccgccaaa ttaaatgtgt cgttatcccg tagatggtag    39360
cggtggggac tgtaaatccc ttgtcattga gactcggtag gttcgactcc tacacggcac    39420
accaataaag gctatgtagt ttaatagggt taaaatactc ccctgtcacg ggagatgatg    39480
tgagttcaag tctcatcgta gccgccaatt ttgagagggc tatttagtcc ctcccttaaa    39540
gagttcttac gagtattctt taaaggagca gaagaccaaa ttcagcaagt acgtatgata    39600
ttttcaagcc aatttaattt tgaaaaaatt taaaacttgg tctggctcaa caaatttaca    39660
gaagaccgtt tacagcaaaa cttaaacaat ctatttctcg gtaaagaaaa ggagaaggtt    39720
cgattccttc actcggcaga tgtcgagttg gtgtaatggt agcacttaag atgataaaca    39780
acggtctggt aattatcttt gcagtgactt atggtgctaa tatatcgtcc catgagtgcc    39840
gatgagtttc cttagcataa ttctagatta gcttaatagg agatgactct acaagccctt    39900
tagcaaggtt tgcgtaggtt actgcaaaga tgatttaatg gaagtgtagc agaatggtga    39960
tgcggcagac ttttaatctg acaggcgatg ggttcgaatc cctccacttc taccaatatg    40020
gttcagtcgc agataaggta atgcaagggt ctcataagcc ctatgaatgt gggttcgatt    40080
cccatctgaa cctccaatgc tgtgaaagca catatggatg tgcattcggc tgataaccga    40140
aaggaagaag gttcgaatcc ttctcacagt accaatttca ataaagttgt tgacattgag    40200
atgtgaccac tttatagtaa ctaaaatact tcataatatg tataattcaa acaccaatac    40260
atgagcgtta gacgtaacac aatgtgggga aatttgttgt acatattctg aatagttttc    40320
gttgcgtagc gtctattttg caaatttaaa ataaatgcaa acgacaatgt ttttctggca    40380
gtagcttgat aggctaaaca ccagtgaggt cttccaatcc ctcatcaaag aatttggcgt    40440
actcgcccac ggtatgatta ataaggtggg caacattcta aagggtatcc cttatggggc    40500
ttggcttaaa tgcaatgagt acccttttaaa atgttaatta cggggcgtat ctcagcggtc    40560
ttctaaaccg ccgttaaccg agtaagtgga gtatgcgggt tcgagtcctg ccgcctcgac    40620
caattttgga tgaaatcatg aaaacttgta ttaggtgcaa acttagcaag gatgaaagtg    40680
atttctacat gaaagatggt aggagaactc attcatactg taaaaagtgt gttaatgagc    40740
aaaccataga aagacaaaga gcacttaaac tctcagctat tgagtacaaa ggtggtgttt    40800
gtcaggattg tggtaaaagg tatcatccag cagtgtatga cttccatcat ttgaatcctt    40860
cagagaaaga ttttaacatt gctcatagaa gaagtcttaa gttctctcag gagcttaaga    40920
acgaacttga caaatgtgtt ttgctatgtt caaattgcca tagggtaaga catgcaaagt    40980
attagttagc agattactta gacgacctaa gcgggtcttc ctgtagggag gtggtctgta    41040
tctcatgttt tccagaacat gtaaataatc tgagaagggg ctttacagtg ttgcgaaaat    41100
acggtaagct tcgaattata gtgtgggacg atgttaagac tctaaggcat gagcaacggc    41160
ctccaaaacc gtttcaaagt ggttcaactc ctccgtccca tgccaaagtc ttattagggg    41220
taggtagcgg ctaatggtag ccaaactgtc ttgaaaacag ttgccactgt agagatacgg    41280
tgagggttcg actcctttac ttaccgccta ataagattta aagccaagct tcattcggat    41340
gttgctttgg tatccctcgt gtattgtcgt acacaagtaa agcacctagt aggtgtcacg    41400
gagaagagat aatatcaagc tctccaaagg ttctagtcac cggattaaac aagactatgc    41460
aaagaccaat ttaggtcttt ttagagggct tctaaggtta ttacagcttg ttgtggaacc    41520
ttgttgctta ggttcttaga agttctctaa aaagatttaa tgggagattg acggtaattg    41580
gtaaacctat ctcgcttaga acgagatgtt tgagggttcg aatcccttgt ctcctaccaa    41640
```

```
attaatgcag gtgtagcaaa atggttatgc ggctgactct taatcagtaa gacgatgggt    41700
tcaattccct ccacctgtac caaatattgg ggatgtagtt tacatggtta aaacataagt    41760
tttgcaaact taagtacagg gttcaattcc ctgcttctcc accaattagt gcatccatag    41820
tttaaacggg aaaattacag tcttccaaac tgaggttgag ggttcgattc cctctggatg    41880
ctccaaacaa tgctgctttc gtataattgg ctattacaca tcccttgtaa ggatggaaat    41940
gcaggttcga gtcctgtgag cagcaccaat tcagaggtca agtgaaagac cgctggtgtc    42000
aactgaagac cgtaacaaat tccacggagt tgagttagcg gcacaacttc agacctcttt    42060
cacactcgct tagtttatat ggtaaaacat caccccttaca agatgaagaa aaaggttcaa    42120
gtcctttagt gagtaccatg ttccagtatc ccaattggca gaggatgcaa gctcaaacct    42180
tgtattagtg acggttcgaa tccgtcttgg aacaccaatt ttaagaggct atttagatga    42240
gatatttgaa gtatgcttca tggatttttcc tagctttgct agaaccatttt gcagcaatcc    42300 tagcagtcat cttagcacct ttcgtagttc cattctacag tgagaagaaa ggacacttac    42360 cttcggctt cagatggatg gagacatatg acaacccaat tgatggtgat aaaggtcatg    42420
tcgaacgatg ggctaagatt agaaagattg gtaagcttgg tgtctatatg cagagagttg    42480
gttggctctg gagaaacaaa gcttataact tctcttacca tgtgttagga agagatgtaa    42540
aagatgttac taagtggaaa ggtaatatca acgtaagctc tgaccctgaa gataatcaga    42600
caggttatct cctaatgtgg aacagtaatg cttggggatt attcgctttt atcccatcaa    42660
ttaaagtctt tggtaaacaa ttctactgga gaatttatgt tgggtggaaa ctaaaaagtg    42720
ttgttccaaa agaaagagca ttctcaaggg aaagagttat gttggcattc tttattcatc    42780
cactaagaaa gtaaagactt aaaggggatt agtttacaag gttaaaacct cggtctttga    42840
aatcgaagaa gttggttcaa tcccaacatc ccccgccaat gctccattac tccaattggc    42900
agagaggcca gacttaaaat ctgtgttatg tatcggttcg aatccgatat ggagtaccaa    42960
atttagcggt atagcataac tggcaatgca acagtctctg aagctgtcct attaaggttc    43020
aaatccttat gccgctgcca cttctaagga ttcttacgag agtccttaaa tgtggcctta    43080
tcataaatgg taatgaccca tgctgtgaac atggtctata cgggttcgac tcccgtaggt    43140 cacccccaatt tatagtccaa gtagcttata tggttaaagc gcgtgtctga aaaacatgag    43200
aagagggttc aaatcccact ggactaccaa tttcaaaggt gctaatgaa agagatgaca    43260 gaacaaggta aggagatttt taatctctta aaaaccggta gagggttctc taatcccctt    43320
attactggtg cagcagttct aggtggaacc gtagctgcct ctacatcact tgtaagctct    43380
attagctctg taacagaccc tacaatgaag gagaagcttg ttgctgctgg acttacaaca    43440
gttctgctta acagctttac aacgagtctg acaagcacta catcaaccac taaaacactg    43500
acagattatg gtcaaaagtc cattgatgag ttttcatcac gtatgcaggt agcaaaaggc    43560
tattctaacg ttatgggtgc agcaggagag caagttggtt gtacaccatt tagtggtatt    43620
atgggtgttg ctacagaata tggtcaaaaa gctattgaca caattaacag tgcactagac    43680
ggtgttaatg atgtattaag tgacttacaa gatgctattg acaaaggtct tgatactgtt    43740
tctgatttag ctaaccaagc tgttagcaag attaatgaag gtatctcgaa gattacagct    43800
tatgcagatg aagttgtgca gatgattgaa gaagaagctg cccttattgc agagtacctt    43860
aaaacgaata tcaatgggtt cttagcaggt atcttaccag actggtttga tgatgcttgt    43920
aagactggtg tgattgacac tattgcaaca ccagaaatga agaacgcatt acagaaataa    43980
tggaagatta accctaaaag gtaagggagc agtttgctaa actgccagta gctgagaaat    44040
```

```
cggtgtacca gttcaagtct ggtatcttcc tccaatttga atccgtgaca gaaatggcta   44100
tgtacctgtc tgcaaaacag gtttataagg gttcgagtcc cttcggattc tccaagttat   44160
tttactctct ctcaattaaa ataataataa tgccctgcta taagtattct tcctttcgct   44220
accgaagagt attttttagac agggcttttt tacagagtta tactttataa gaagactgat   44280
acagtatgtc tctgacgtac attgtggttt ctccttgacg gtctctgtgc cgtctttttt   44340
aaggggaaac agtattaatt atttggagaa aacataatga gcgagaccgt ttataaagaa   44400
ctttatgaag ccaataaaaa gctagaattt atgcagacta ctattatggc aattgcagac   44460
agattatctg tagcaacagg tattgatatt aaagaagcat ctatggatgc acttcttgat   44520
gctgttgatg caaagttcga agttaagaaa gaagagactg ctacagactc tgaataattc   44580
tatttgcgga ggtgcttaat ggacttaaat gctgttaagc agaagcgagt ggaagatgtt   44640
aggaaagtcc tagctggaga gttggggctt tctgatgaag taaaagaaat tatcaaatca   44700
ttcggtaaag acccctctaa attccttcca actcaaattc tgactttatt aagatacaca   44760
ccagaccaag ttagacttat cttcaaattg atgactgata agaattatgt agcccctcag   44820
ccgggttctc aagaggtctt tttaaatact aatgctgact tggttcttta tggtggtgct   44880
gctggtgctg gtaaaactgc tgcattgtta atggactctt taagatttat tgaagaccct   44940
aactataatg ctgtatattt ccgtcgaaat acaacacagc tacaaggtgg tttatggcct   45000
gctgcaaaga aactatttgg taagtttggt gggattcctc acgagcagaa aatgactatc   45060
acattccctt ctggggcgac tatcaagttt acctacctag aacttgaaaa gcacgctgaa   45120
ggtcatcagg gtattgaata ctcagctatt tactttgacg aaggtacaca cttctctgct   45180
tcacagattt catacctaca aacccgtcta cgttctggtg ctgaaggcga ttcatacatg   45240
aagatttcca tgaacccaga cagagaccac tttatttacg attgggtaga accattctta   45300
gatgaagaag gttatccaga ccctgaaaag tgtggtcgta ttcgttggta tgtaatgaat   45360
gatggtgtga tggtttctga ttgggagaga gacaagattc ttgaaatgtt ccctcttgag   45420
attcctcaaa catacacctt catctctggt acgattgatg ataacccaat tcttgacttc   45480
ttagaaccta agtaccgtgg taagttggaa acaacaccc ctgtaaacgt tgcaagactt   45540
cgttttggta actggaaggc tcgtgcagaa ggttcaaact attggcaaag acaatggtgt   45600
gaaattgttg attcactccc agaagatgta ttcgatgtca gagcatggga cttagcagca   45660
actttaccat ctgagattaa ccctaatcca gactggacag caggtgttaa gatgggtaaa   45720
tctaaaaaag acggttgcta ttatatcatt gatgtagtaa gatttagaga tagaccctct   45780
ggagtcgaaa cacaaattaa tttgactgct gaaagtgacg gtaagcgaac tggtatttt   45840 atccctcaag acccaggcgc tgctggtaaa tcctacgcaa catccctcat caggaaactt   45900
gccgagaaag gttatcgagc aagggctaaa ccaacaaata agacaaagt tacccgattt   45960 gcggggtttt ctgctgcttc tgaagctgga cttgtaaaag tcttgagagg tagttggaac   46020
gaagcttact tccaagaact tgaaggtttt tgtggtgatg gcaaaaccaa agatgaccaa   46080
gtggatgcta ccagtgatgc tttcaacagt cttaacgaag ttaaattatt caagccacca   46140
tcaatgggtg ctcacacaga cttagtgaga ggaaacccat atgaggggct tagacgttga   46200
tagctaggtg agaagaatgg cagaaattac agaaacacaa gaaagcttac caccatttag   46260
aatgggtgaa gtaggttctt tgggtctgaa ggttaagaat ggtagaatct atgaagaacc   46320
tcgtcaggca ctaaggttcc ctgaaagtat taaaactttc caattaatga tgcgtgaccc   46380
```

```
tgctgtagca gcatctgtaa atattattaa gatgtttgtc agaaaagtca actggagatt    46440
cgtacctcca aagggaaaag agcaagaccc taaaatgctt gaaagagcag acttctttaa    46500
ttctttaatg gatgacatgg agcatgattg ggcagatttt attaattctg taatgtcatt    46560
ctgcacttat ggggttctgtg ttaacgagaa agtttataag aagcgacagg gtaaaaaagg    46620
aaagtaccag tcaaaatttg atgatggtct aattggatgg gctaaattac caatcagaaa    46680
ccaatcaaca cttgataagt ggtatttttga cgaagacttt agaaaagtta ctggtgttag    46740
acagaatctg agaaatgttt cacatattgc tggagcaatt aatcttggag aaagaccatt    46800
aacaagaaaa ctcccacgag ctaaattcat gttgtttaaa tatgatgacg agtatggaaa    46860
cccagaagga cgttcaccat tacttaatgc ttatgttccg tggaagtata aagtccagat    46920
tgaagagtat gaagctgttg gtgtttcaag agacttggta ggtatgccaa agattggttt    46980
accaccagat tatctggatg aaaatgcaga acctgaaaag aaagctttcg tacaatactg    47040
caaaactgtt gttaatgata tgattgctaa tgacagagca ggtttaatct ggcctagata    47100
catcgaccca gatactaaag aggatatttt tgagttctca ttagtttcta gacagggtgc    47160
taaagcatat gatacaggct ctattatt                                        47188
```

<210> SEQ ID NO 2
<211> LENGTH: 20949
<212> TYPE: DNA
<213> ORGANISM: Artificial Sequence
<220> FEATURE:
<223> OTHER INFORMATION: Novel Bacteriophage CJ26

<400> SEQUENCE: 2

```
ggacgtacct taacaatggt gttggtagga ctatcaggat tgcagcagca aatggttcag      60
atgttgctac aacaggtggt tcagactctg tggtgttatc tgttggtaac ttaccatcac     120
acacccatag tttctctgct acaacgtcaa gctttgacta tggtacgaag acatctaaca     180
gcactggtgc tcatacccac tcagtcagtg gttctaccaa tactactggt aaccaccagc     240
atagtgtagg tggtcgttac ggtggtgact ctatcggtgg taaacaacgt gttcaggtag     300
aagggacaaa ccagatttca agtgttgctg gtgaccactc ccacacacta tcaggtactg     360
ctgcatctgc tggtgctcat gctcacacag taggtattgg tgctcatacc cacacagtat     420
ctggtaacac tggtggtaca ggttctggtt cagcatttag tgttactaac cagttctaca     480
agttaatggc ttgggtaagg actgcttaat ccattgttga ctgattgtta agatggtgtt     540
aatattcttt ataggtattc tcaccatctt ggctggtaag gtgattaaat gcctacaatc     600
ctagcaattc ttctaaaaaa tctaggtagc ttcttctgga aactcatttt atcccttcta     660
agtgaataca tgattgagaa agtgttcttt aggcttgcaa gataccttgc gagtaaaaca     720
gatacaccta ttgatgatga gttcgtagat aacttagaaa aagcttttaa gggggagaat     780
aaatgaagtg gctagaggaa gcttttaaaa acaatattgg tgcaattgta gttggtattt     840
ttagtgttat tgggatgtat accacaatgc aggttgcaag tggtaaacaa gaagtgtctg     900
tcacaacaaa gttacagcag ctagataatt attccaaaag taattattca gctattcgtg     960
atttgcagtc tgacatgaga ctgcttcagc tagggatgga gaatcagaaa gttcagttag    1020
agaatgttaa gggtgagaac gcaaaactta ctaagactct tgataaattc tctgacagcg    1080
tgaacaatct ggctcaatca gtatcagcct gcaagctat tactgaaaag aacacaaaga    1140
atactgaaaa gtaaagttta aggctcccgt aaaaaggagc ttttttgtt ttatttacct    1200 actgataaag gtgcttcaat ctttcctgca tgttggtaat tattaatacc accgataaaa    1260
```

```
tcacttgcag tgagatgttt taagtcactt aaagtgttaa gtgggatacc aatctcaaaa    1320
gttggtgcat ggaactcttc attgttcatc agttcataaa cctgcttcat gtggttctga    1380
taaatctgag tatctccaaa gacacctatc aagtaccgtg gagtgtatcc agtcatctta    1440
caaagaactt ccagaataaa accataggat gcaatgttaa atggaagtcc taaaaaggtg    1500
tctacagaac gctgatacca ttgtaagtca acttcacctt cattagtgat ataaatctga    1560
aacagaacat gacaaggtgc taaagccatt gagtttgctg caatgtctgc tgcattccaa    1620
gcattaacaa gcatgtaacg gtctgtaata tcacccttca tcttcgttac taaggtctct    1680
agttggtcta caacacaacc attatggcct tcaaagtttc tccactgaac tccgtagatt    1740
cttccacctg catcgtctaa ccaatcctgt tcagaagaat aattagagct taaccaacgt    1800
ttaaaatcat ctgaccagat agtccagcgt tccccatcat tttcatccca agtacggtaa    1860
cggagttcac caagtttatt ctcaccattc aggaaccata aagcttcccc aataacttgc    1920
cgtgtaaaca cctgtttaga tgttaagagt gggaaaccag ttcgcatatc aaaacgaaac    1980
tgaggtggag caaatgcaga gataacatct ccagttcgtg tagtacgcag ttcaccaact    2040
gataaaaacat ggttcaggat attttttgtaa cttgaatctg cttgtgacat atcaaaagtg   2100
cccttttact tgtggaacat aaatttcaaa agttgcttta ccatcctctg atggttttga    2160
ctgtaccttt gtaaatacac ggttatcata cagcttctca aagaagtttt caaaaggtaa    2220
atacacagtg gcctcttcag taactttatg gaaaactgta tggaaaacta catcagcata    2280
cggcaaagca tcaacaagga cacctgcacc accaattaca aagacatctt catcaataga    2340
gctatcaaga tacttcaaaa atgctccaaa tgactcttta ctggctttag catacattac    2400
atcgtctttg ccaaagtcta tacctaagta tggtacagag tttgttaaga tgaggtttgc    2460
acgttctggt aaaggtttac tacccagagt cttaaaagtc tcattaccca taactaccaa    2520
gttgtcttta gtaagcctct taaactcttg catatcctgc ttatgtcgag gccacggcat    2580
accagttgga gtaccaaact ccccattttc accacttgca aagattaatt taatcatttt    2640
gtaaaccctt tcttaatgaa ccagttgata acattcttca cagctttatt actatggtag    2700
attaagtgtg gtgtaggttg gtataaacca taagcccaga aagcaatgat ttcattacac    2760
cctgtacacc ttgtactctc ttcagcgata tgaccattga ctatttcact tacctcacct    2820
tgtaagtctg tacacccaca atgtggacaa cgtataggtg ttccatcaga ctcatagcag    2880
tgttcaattt tcatttattt aacctcaaaa actggctcaa gaaccaatat aaagtctaca    2940
cagtcatctt cttcatccag aataccatca aagttcttag gaacgaagtc gaagaggctc    3000
ataacaaaac agtcagaagt aacccttata gtgcctccca tgttttctac agttaacact    3060
gtacgacttt cttttacctc tcgcagaaga ttgctcacaa agtcatctaa gaaatacttc    3120
atcagtgact taaaaccttt agggtaatct gtaccagagt atgtttcaat ctgaggtaca    3180
agcttaacat ttataccagt cttttgttaag aatgtattag agaacatact atcaggtaac    3240
ttgcaaacag tcttcccagt accttcatgt tcaatctcaa caaaaccagc ttcgtcgcca    3300
catgtaacta ttttaaaaga tgcttcattc tcatactgtg aagccataaa cttttttaagc   3360
atttccttaa ggaaatctgc atgagcatct tgtaagtaga tatcaatcat agttaatcac    3420
ctattatggg aacagacact taatgtcatc attttttgaaa acgaagcttg tgtagttgtg   3480
accgtcaaca tccagccaaa cagcctgaac atctacacca tcaagattgt ggtaaagttc    3540
tttgatgaag tggtcttttta cagtctgact gctagttgtt tccagcttaa tgtttgagat   3600
```

```
tgctgaacct acagccatat aacccatgac acgtttcttc tcagtatgct taatcttacc    3660
atctttgtaa gccataatga gattggaaag aatctttaca ccataatact tttcaaggtg    3720
agtaggcaca ccataaaaac ctaatgcgaa gttttcagag tggataatgt tttcacgttt    3780
catattaatc tgccagcctt aaattaaagt taacaccaaa ttttcacat acttccaaca    3840 taaactcaag ggagacatta ccagtgagat tgattatgtt ggatacacga gcctgagaga    3900
taccacaaat tttagcaact tgctcttgag aaagacctct ggatttaatc tctctcttaa    3960
aacgatgtgc aacgaaatct ctcatttcgt ctacatccat tggacaaata taactctcca    4020
tttcagcctc tctgtcagcc tcccaatcat cttgtggagc ataagggtca aaaacctcat    4080
tcatctttct tcttccgttt gcgtgaagtg tcaatcaatg aatctatgtt tgtagctcta    4140 acctttcac gttcatcgtt aagataatca tcaagagcct tctcaatctg tgaatcatct    4200
tgacagataa ctgtaaagac tgtaaagccg tctgtatcat caattatctt accataaccg    4260
cttctgggat gtaacttttt aagagccata tcaaatacct gtgcagcttc tgttttctaa    4320
gaaatactca acaccataca tagcttttttg catcaaatct tctttaaact ggatacgatg    4380
attgagcata gtctgtacat caatatcatc atggtgtttc tctttaatat ttgcagattg    4440
caggaaatat tctgcaagaa cacgatactg atagtcagtt accttatcag tcatctctgt    4500
caaagactct tcagagatgg gtttaagtaa ctcaccttta gatagcgcaa cacctttaac    4560
aatctggcaa gtgtcttctg gaacacctga taagtccaca tttggaagtt ctgttgcatt    4620
gactggtaag ttcattgcca taaccattgc agcagctaat aaaatctttt tcataatgac    4680
ctcaaagtta tattaaattt tgtattacat tgagtataaa aataagctat aacacctgac    4740
ttgtcaacag actttatagc ttatttggca gatttttat aaggctactg ccatccttcc    4800
ataccaaacc atacctgacc ttaccagacc caacctagcc atactgtacc agaccttatt    4860
aaaagaccct cttaaagacc ttttaaaaag gtaagtctaa ttttaatgta gctgagacta    4920
actacccata ccttacctca cctgacctga cctgacccta cctagcatta ccgtgccaca    4980
cctcacttaa aaaccctctt agaagactct taagtgatgt aatcggattt ttatgtagtt    5040
ccgattaact acccatacca atcctaacct gaccgcacca aaccttacaa caccacacca    5100
tacctgacca taccaaacct cattaaaaga ccctcttaaa gacctttaa aaaggagcct    5160 ccgaagaggc tacctagtca acttagaaag gttttctacg ttgcttgtta atgttagctt    5220
tcatagcagc taagtggttt tgctgttcaa tcagtcgtga gcgttcttga tggctaagtg    5280
ccatagtatt cacattctca atagcttgag tggcttgctt taaagctcga ccaatcttac    5340
cagacatttt acgttttgca atagttgctt gatgtttagg ttcaaccaca cgataaccaa    5400
cacccattga agcaaccaga taaatcttct cttctttaag aagcttctca ataaacttct    5460
caagtcggtt tagacgtgta agcgcataag cttcatttc atcttcgtac ttaacaatgt    5520
caccttgata agttggcttc acaataccta agaaggtgtc catctcagaa tgtgataccg    5580
tgtcaccgta actgaacttt gctgctaatg cttttgtatt cataattaaa cgttaccttc    5640
tgaaataact tctacagaaa aacgaccaaa gcgtggacgc caatcaccta caccacaaag    5700
gttaccagca ttttccagaa ccatcagaag ttcctctcgg gtgatttgct cttcatcgaa    5760
catcaaacca aactctacag accagtcacg gaagattgga cggtagctca taactcgtgc    5820
tgtgccaatt taacagatt tagcatagat aaagtctgga ttcttagcaa gttcttgtgg    5880
gtttgctgga cagttcttga tagtcattgg gaagactaca tctgtcagca taatggctcg    5940
gtcaattacc ttaccaagtt tgttgagttt tgcaccagac ttaatacaag cctcaatcat    6000
```

```
ctcaccgttc ataacaaaac caagttgctc atcgtagtaa caagaagtta ccagttggct   6060
ttctgctaag agcgcatagt cttcgtcagt cttttacgt ttactggaca aagacttgtg   6120
atatttcgtc agagggttta atgggtctga cagcgtatcg ttatggctca agaaaggacg   6180
agtaccagtg attttgacat ttaacagttt catagcattt agctccacac tttagtttat   6240
tgttaagttg tttgtaaaga accctcaaca gaagactctt tagaaacttg gtagattttt   6300
aacgtggcta ctaccatcca cccacacact accttaccgt acctgacctg acctcacctt   6360
gccctacctt accttattaa agaccctgt ttaaagacct tttaaaaagg taagtctcat   6420
tttaatgtag ctgagactaa ctacccatac cataccttac accgccgtac cacaccgaac   6480
atcaccaaac cataccaagc cagagcctac tgtaccatac cgaacatcac ttaaaaaccc   6540
tcttaaaaga ctcttaagtg atgctggtga gtacccgttg gtttatgctg ctcagtatac   6600
tcaccaaatt ttctatgtca acaactttt attcataatc cctaataact agcccgacag   6660
ggaactgtaa agaacccta cgagtcatct tctggaactg tactgttaaa ggcttcccga   6720
taaactcttc aggatgctca gcaagatact gtttcttctc atgagtagtc ttccatgaga   6780
catctacaaa gacgttagga agagtctcta caacgaactt gccatgacca cgtttgtcag   6840
tctttacacc agtcacttta aattcttcag tgtgcatctt cttgtgctta atcaagaagt   6900
atgaacggtg acaacactca tagaaggagt cttcagagat tgaacggtac attgcacctt   6960
caaacttagc ttcaacccac ttatcatgag cttcatcaaa ctcttcccaa gaatttacac   7020
gacgagattt aacaggaaca actttacagc catctctaaa gtcattcaat ggtgaagtct   7080
caataatatc tctacgctca ggccacgtct tagtactatc acagatatcg taccagtaga   7140
actggagtag atgtcggtct ggattgtcag cattcttaat catagacaca atatcttcta   7200
agtcccaacc atgagcataa atctcaccat caaagtcttc gacttgtgga tgcaattaa   7260 gcaacaaag caaatctggg attagttctg ctgggacgtt gtaaatagta ttctcacgag   7320
aataagccgt gaagctaact aaatcagcat ctcttgaaat cctacaacgg acaccatcaa   7380
gcttcggttg agcatcagca gggaatttca aatactttgc gtgactaacc tttgcagcat   7440
catgagcaag ctgcacacct accttctcag tattctgtgc agactctttt gtgtaagcat   7500
agcctttgcg gtcaacttgc ttttatact tagcagcaac ttcaaagaga gcttgctgtt   7560
ccgcattacg ctcattcttt ttaccaatgt tcttcggttc tgctgtgtac tcttcaaaca   7620
tcatcttgcc gttctctttg ccataggttg tgataactt gtcacctaca gcaacacatg   7680
accagacatt gaaagaacca tctttatttt gtttgtacag aattgtcatc tttaacctct   7740
gagtgatacc aagtgtaaca agcattacat gcgtaaagct ctaagtcatt tttatctggt   7800
ttatggaaac agtttgaccc acaacgacac cgaaataact taccatcaac acgaagaatg   7860
aatgtttcaa gctcaccatc ttctgtaaga actgcgtttt taaatttatc ttctacggtc   7920
attttctctt accaccaatc tctacgtcga taacctgaac atcaccagca acatcaaact   7980
tatgaatgat gctttccaca gtgtaagtcc aaccctcgat gcgaaccaac tcccttctc   8040 gtgggacgat tggattacgt tgagctacgg ttgtagtaga gtgaacaaca tcataacagt   8100
agatatagtt tactaggact tccatcgtga aaacctcact caataaccgt agtgtgtgat   8160
tgaccatttt tgccatagct ataagatgtt gttgtttgag agtttggaca tctgacaaca   8220
acaatatctc tgcttatggc gtcaccatgt aacttataga ctttgcaatc ttgcatctcg   8280
ggtgggaggc tataagaagc attttatct tcataagaag ggttgcagcc agctagaaaa   8340
```

```
ataacaccaa gtacaattac tgatttccac ataatacttc tcctgtctgt tggtcacgat    8400
actcaagctc tctgaaagtt ttgtagtaat gtgttttgta gtgtgctacc tcattacttt    8460
ttacgtttgt ttttagcagg ttccaatcag agtctttacc catccttccc cagaggctat    8520
ataacctatt cataacaatt ccaaaatatc aatacgttca cccttgagta ctcctgtgca    8580
atcttttgca atcttaccat caacgataag aatatgcgcg acctttaaag cctcatgatt    8640 aaaaccttttt acgaacttac taggcataac tacaatggac atctcctgaa tcaactctgg   8700
agtgtagcaa ttatcgtgaa gttgctgaat aacgtctgca agtgtcattt ttgatgtctc    8760
caacactcaa tgtcaataag ttcttgtgca atgcttttca gattaccttt caagaaaacc    8820
ttctcagaac ctgacagaga tgaattgtca attaacctgt tcatcctctc aaacaacttc    8880
tgtttacgat tcttgatagt ttcctttgaa gcacctttca tcattgctgc atgggttctt    8940
ccacggtggc tcataagccc tcctatataa gatattgtat aaggtactct tccatgagca    9000
ccttgtcaag atagttttgc aaactctccg tggagtttta tagcagcttc acagtaagct    9060
ttatgggctt cttcaggtgt gtcatgataa cctaaaaaca tcttcttacc tctataactt    9120
atctgtgcga cccacttacc agacttcttc ttaagactta cacccttgta cccagattta    9180
ttggtgacta gcttaccttt attccaagca ctttgaaagt catctgcttc ccttaagttt    9240
acaatcctgt tgtcaagtga gtctccgttg atatggtcaa tgatacctttt tggcatcttg   9300 ccatacacgt aaagccatgc gagtctgtgt gctttatgtg cttttcttgtc aaaatagata   9360 ctaatctgtt tatgaccact tgaatcagtc tggatattac ctgccacctt tcctgcataa    9420
ttactgttaa aaacactaac agctcttgat ttaccttctc tacgaagcca agtaaagacc    9480
cctgtttcgg ggtcatagtg tagcagctcc tttaaacgtt tttgtaaaat aaaatccatt    9540
aatcaatgta cctcatacca gctcttacca acctttgctg taccagttac aagtgtttct    9600
ttcctcaaac ctaagttttt tgaagcttgc ccatacatcc agtcagcaat gctttcata     9660 tcatgtgtca taccctctgg gcattcccaa ctattttcgt cgtgatatgc cagaagtaac    9720
cttgctccga tagctggttt tcgagcattc agttttgtca gaccatcttc acaggctttt    9780
cttgctgcta ggttgatggc ttcattctga atctgtgctt ccgaactcat caggaggtag    9840
ttcagtagtt tatgtggaga tttgcaccat atccatgctc cagcgaccct gatataacca    9900
cctttagcaa ttgaagagtt cttcccaaaa acctcttcca gagccttttt agacgcctta    9960
aaatcagcct ctaagctatc aagtaacttc ttaatctttg gcaaacgcat atagtaagtt    10020
tgtttagtca atgcaccttc ttccgtagat gatgccttga tagttttttgc aaacttctca   10080 tcgccagccc cgaacaatac atctggtcaa tacactcgca aggtgtacca gttctcttat    10140
gaacttctcc gcatttctac ggagtgtcgg actatatcac gtagcagtga tgctaccgtt    10200
gcacttgggg atggtcatta gcttaccacc ctactctact cagttcatac gttaagtatg    10260
cttttcgata gtctctgaac gttcctctta agaggcttcg ctgctgatta ccatatcttt    10320
ccagacttag gcttccagca attcacaacg ttttacatgc gccactgacg cataaatgcc    10380 attttttggct ttcttacgac cttttgtaat ctcgtgaaga agctcctcat cctgcgtctc   10440
cctacaacga acaatatcat cttccttgtt tagaccaaag taaatactat tcagtgtatg    10500
tgcatcagta cctgtgtaga cttcgtagag gtcattctca gcatcataac gaagatactt    10560
atcagtttct ggattgaggt acttatcaag atgcttgcaa tagtatctcc catcctcttg    10620
cttggtaaat tctactgact cttttaccttc agttaccgct ttggtgaagt ctttatcacc    10680
cataaagtta cacagtaaaa caagctgtgc agagttctgg tcaactgaaa cgatattagt    10740
```

```
cccttcctcg caaatccaca cctccctcat aggtgctcca tagacagcag caccagacgg    10800
tacgtttaca ataccatatt gtgtcatacg tccagttgaa gtaccaaata ccattgcacc    10860
agcactaagg cgaccatctg gacgaatctg gttcaaccaa ccttttcat catcctttga     10920 gttctcaata gttctgcgtc tgtgcatcaa agtatagtac ttagcaatct tctgtccaag    10980
ctcaccttca attgtatcat aagatgattc agtaagtttt ggtgaagtac ggattaagca    11040
aggctcaagc aaatctgtgt atttcttcac agaccagtta tgctcgatgt actgaatacc    11100
ctcgtgttca acataactca aaccacaccg ttcaaccatc tcctgccact taggatgctt    11160
tgtaatcatc tttttgttgt ctttgaaacg acaaactttg acaggacgac cgtctgagtc    11220
tttcttatag ttccagtcat ctggaatcca accaactgat ttcaagtagt ctttaacaac    11280
tgctacctga gtcatacgag aaacttcgaa ctcaattggt gtatatggtg catcaatcaa    11340
acctgtgtag cggcttgact caagctcaaa gtggttaaca acatgactgt tgtagtactt    11400
cacagtttta actgttttta ctggcttcca gtctttgcat ttcttaccaa tctttgcatt    11460
caactcattg caaattgcac gagcatcctt cattgctaca aaaccttcct tgtactcttc    11520
accagttaca gagttggttg gtgtatagca attccgcttt tcaatgttaa aaatctttgt    11580
agttggctta ccaaatggct tgatttcgta tgtctgcatc tcaccgttac gtacctgttg    11640
acgatacttt gtcttagggt acttggtaat tctcttcagt ccatctgcat gaccgaatgc    11700
ttcaacatac tcattccaag cttttgcaaa ctcttctcca gtgactttac ctttggtctt    11760
aatagttgga ggaagatgtg gttcaacctc tgaagcaagc tcattagtca acttgtcaag    11820
ttcctttaca tggaactcca taagttcttt atcagctttc caaccattga tagcctgttg    11880
actcatccag aaagatgttt ctttagctcg catgtaggtt tcataggtgt ctacgccaca    11940
cttctttagc ttgagatatt cattatccag tgcacgttta gttttggcgt taatgcggat    12000
atcttctaca acacgagtga agatttctgc attccacaca ccccaatgtt caatctctgg    12060
tttacgtaca cccacacgag cacccccatgc agccaagcca tgagcacctt tatagccctt    12120
tggagttggt ctatccatcc actgaacacg ggactggata agagaatcct gaaagaaatt    12180
actccacggc ttcactttg gattatcaaa gttccacaaa tcaggtgcaa tgtgattgaa     12240
aacccaccag tcatatccca gaccattatg gatgcaaagt cgttttgcct ttaacgcaaa    12300
ctcaacacct tcacgcaagc caccctt aat gtacttggta tacttgtgac cgaggatagg    12360
ctcatctgta aagacccata cagggggctc ttcatcgtca gatttatagt ctgcgaaagc    12420
cattacgtgc accttagtga actcaaggag taaaccatca gttctgtat caccaactaa      12480 atgtaagttt ttaaaatcta cgttttccat ttgtactccc tctaattcat taacctcata    12540
cattactgca aaaattata aaagcaagt tgacaatgta cttgacaagg tgttaatctt      12600
tgcgaagtgg gttttact t aaaaggttac ttaacagttt aactatacag atactttaaa    12660
actcttaaaa gattatttaa tagcttttaa aaagctttaa agtataacgt atagaatacg    12720
ttaagataaa agattaaaac ttaatagtta cttaaaagag gcttacatgc agaaaatgtt    12780
tgttcaccca gacatagctg actttgttag agctttgcag aagttggaag aacttgacat    12840
tgctgctcaa cgggaatatg ctcaccatca caggagaatg gttgatatac aacatgagat    12900
agagttgtct gaaaactatg aagatgactt aaaatgctct gtatttgagc atatgaaaga    12960
tgttgctaca gcgaggcgta aagctaaaga cacagttgct ttactagatt ctcttaaaaa    13020
gaggttgcaa agtggtacag acctgtgtaa tctagcgtca ctgattaacg atgttgaaac    13080
```

```
ttcttgggat agacattact atccacgttc tgaaaagaca cttgactttt cttcatcaga    13140
aaacttaaaa tgttctagaa agaaacttaa ccaactgaga gagaaataat atgaacacta    13200
ctgtagacca aatgcttaaa gaaaaggta ttgacgaagc attcttaatc aatgccgtag     13260
aaagcatggc tatgattctt cgtggaaaca actacacaga acggtttatg cctgcaagct    13320
ataacttgcc taaagacaag tctgataacg gtgcttttgc agaacaggtt aacatgatgt    13380
tgacagacac ttcactagct ctggcatcta tcgctgttgg tgttgacgca cttgctgagt    13440
tcatttttta tgaaatgcaa aagaatgact atatcaggat gtcagacgaa aataaagaac    13500
tgttgctgac tcaggataat gattccctta ttgatacaat cattgcatca acaagtgctg    13560
ttatggctgc tcttgagaag cgcatggaag agaagctttc acgatatgaa aagtttgatt    13620
ggggtgtaga agagttaacc ccacgaatca gagagattat ccagcaaact aaagagtctt    13680
tagaagaagc tgtgaaagat gattctgtag ctgatgtaga accactacag gtgaaggtcg    13740
ctctgatgat tccagctatt tctacaatga tgaatatcgt tgcactaatc caactttctc    13800
agatgttggg tgtaaccatt gagttcgttg aggagatgac tggtggtgtc agtatgcaag    13860
caatcaatga tgttttggta acattggtg cttcaatcat tgaaaagaag cttcgcattc     13920
actttggtga cgattttgtg aagcaagtct cagctatggc tgaaaagag cactcacaaa     13980
ttactagtga acaacttcac taagcattta taaatcttac aagcctcctt aattggggc     14040
tttttagtaa ttaatggaga taaaatgagt aatattatcg catttactgg aaaagcacgt    14100
tctggaaagg atacctcatg ttctattgtc aagaatatct tagaagatga gtatggctac    14160
aatgttgcag taatggccta tgcagacaat cttaagctat ctgcatcaaa gatatttgac    14220
ttgacatgga atgacctta cggcgaaact aaagagactc cacaggtttt tgatttagca    14280
tactctgaac ttatgcctaa agttacgaaa gctattgagt tcaccttcag agatgaacgt    14340
taccatatgg actttaagct tatgtcagag ctaacaggac gattaatcat ggagcttaag    14400
aaggtcgcta aaccgaccat attgacacgt ctggggttta gtaaaaagta taaattctca    14460
tcaaggcaaa ttcaacagat ttggggcact gaagttatcc gtaaagttat gggtgacaag    14520
ttctggtcta aagacctcga aaacggatg gttcgattct ttgaatcttg ttcacttaga     14580
aatcaagaag gtgttgtttt aatcagtgac ttaaggtttg actctgaagc tgagtggttg    14640
agcagatttg cacaccaaac tattgaagta aaaagagaca atgtggataa agtttcatca    14700
catgtttcag aaaatggaat ttctaccaaa tatgcgcgtg acattatcca taataatggt    14760
actcttgaag accttgaaag caagctaaga gctatcctga aaatttaaaa gagagaatga    14820
agatgagagt aaaagataat tttaaagtta ttgaccatcg tttagtggaa ctctcatctc    14880
tttccgatga ggtaatggtt gaacgtctta agagagttga atcacgaagg aaagagattg    14940
cagatgaaat tcatgaactg acaagattg aaaacggatt gaaggcagaa ctacaacgaa     15000
gaggtgctaa tgtctaaagg tcgtaaattg aagaggctg gtcagtttat tggtcattgt     15060
gcatgtccac gttgtggttc atcagatgct ggttcaatct atcatcatga cgatgattct    15120
tattcaatga cttgctttag ttgtaacaaa ggtttcccag agtgggattt tgataaagga    15180
caaatcgtga gcacttattc tactggttca gacaataaaa accgtacttt ccgtggaatg    15240
gatttagacg atgtaaaaga aaacctagaa gcaatggact gaaagatag gaagattcct     15300
gcaaaagttc ttgagcgttt aggtatcaag gttgacattg acagtgatgg tgaaattgac    15360
gcacatttct acccaaccta caacgtaat gaagatggca agctagaaca tgttggctac    15420
cgtgttcgtc accgttatcc cgaagaccat ccaaaagaac acctacgtgg taagctaaaa    15480
```

```
gacttctcag gtggtgttgg agacattaaa ggtgaactgg caatgttcgg ttcatggatt   15540
gctccagaag gtggtaaccg tttattcatc tgggaaggtg agatggaatg tgctacagca   15600
atctacatga cttctctggc aattaaagat aagtctcgtc gtaagaatta ctgtcacgta   15660
tctgttccat caggtgcaaa cattaagtct atcaaagaca actatcagta cattacatca   15720
tttgatgaga tttacttgtg ctttgataac gatgaagcag gtgctaaagc taccaaagag   15780
gctgctggta tcctacctat tgagaaggtt cgtttattcc agtatccaga aggcgtaaaa   15840
gaccttaacg aatggtggac aaagttctat aaagagaaag atacagttct ggaaggattt   15900
aagcagcgta tctacaacgc acctcgttac tgccctgctg gtatcaagaa cttcgcagat   15960
ggttttgagg caatgaagaa tcgtggtcag attccattga ttcctttccc agaatctttc   16020
ggggatttga acaggttgac ttatggtggt tatggtttag gtgagattac aactattgca   16080
gcaccatctt cagtaggtaa gtcagcttac actcgtgaga tgatttattc agcttggaaa   16140
gaaactgatt ataatatcgg tgtaattcct gtagaagata cctatgaaga gttgatggag   16200
atgctctgtg caattcacct gagcaaacag atttctgaga ttccttatga tgaacgggat   16260
tgggatgaat taagggagc acacgcagaa ctgtctaaag gtcgtcgtat ccatatcgtt   16320
gaccatcaag gggcaattga ccaagataac ctactagagt ttgttgacta tctggttaac   16380
agtttagact gtaagattat tattcttgac cctattacgt tggctctgtc acgttctgat   16440
acagatgaag aggaagtctt atctgagtta ttgcgtcgtt gcaaacgcta ccagtatgca   16500
caggtaaacg tatgtcacgt tcgtaagagc gcaggtggtc agaaagccaa ctctgaaggt   16560
ggagatatct ctgaagagga tatcaagggt tctggtgcgt atttccagat ttctatgaac   16620
aacattctgt taatgcgtaa caaggttgac ccagacccag ttaagaaaaa cttgacaaaa   16680
atcaagttaa ctaagtgtcg tcgtcatggt aagtcaacag gtattgctgg tcatacttgg   16740
tacaatccag atacaggacg tcttatcaaa gcttctggat gtggtgttga cattgatggt   16800
gcagcagaaa atattcgaca acagtttggt attggtgaag ctgaagacca ttacgatgac   16860
tctttacctc attatgagga tgaagtgttt gaccgtgaga ctggtgaagt ctatactgaa   16920
gaacagcgtc aaagctcaac gattccacct gtattaagtg aggatgcaga tgactgccca   16980
ttcgaaactg agtgatagtt ataaaagaga ggggttcaca cccttctttg aagaaaaaag   17040
tttaaataaa tttcaggaag agtgtttgac aaaggttgat aggttctata gaatgctcct   17100
catgaaatgc aatggagaag ttgagataaa agaagatttc taccaaagca cgattacagt   17160
catcattaca ctgcctcagc ataatattag ttggctgttt ataattaaag aaaatgtgtt   17220
tgaatatcaa gtatatcgga gaatatcatg aaacactcta aagcatttga aaaagtttt   17280
ggggattcct taaaagccac tgctggaaaa ccagcaaaat actatgaaga gaagcgtgta   17340
agaactggaa aaactgcacg taaagcagct tctaaagata agcacaactt ccagtaatta   17400
atgtttgaca atagagtatc aacaaattag aattggtact cttcataaat tgagatagag   17460
gtttaaataa tgtctaaagt tgttaaaatg aaagctccgg tagagaagta caatggtact   17520
gaacgtcaaa ctctgcgtta cctgttgaaa gatgtttggt tttattacct gaacacttca   17580
ccacgtccgg caaaaggtaa atccattgat aagaaattcc caggaaaaga ttgtaactac   17640
agtgttttcaa ttctggcaga agatggtaac aaactatttta aagagtttac taagtctaag   17700
aaaaacccag aaggttggga taagttact actgaagcag ttgatgcaga tgacttcgaa   17760
gagaagtttg gttgcaaacc accatttgaa gcagacactt actacatcct gaaagtaagt   17820
```

```
cgtgcagcag cttataaaga tggtgctgta tggacagcta acagtcatt  ccctgtaatg   17880 ctgattgaag aagtaaacgg taagcgtgta gctgttaagc agccgatgaa gaaaatcaaa   17940
gctcaagcat ctgataaaca tgaagatgac aagaactatg atgtaattca cccagatatt   18000
gcagttggta acggttcttt tggtagtgtg attctttcta ctcacttcta cactttttgag  18060 aacaatgttc tgacaaaacc tattcaggaa cagtttatca ttgataccct tgtaccttac   18120
actggcggta acggtgctaa tggtgaacct gaactggatg aagatgaact ggctatgctt   18180
ggtcttgatg gcgttgaaga taacggtgaa atcactgaag aagacgcaac agaccataaa   18240
ccttcgaatg cttctgatga tggtgatgat gaagatttgc cagacccaga tgacgaagaa   18300
gatgaagact tcgatacaga agactaatct ctaaaagtta cttttaaagcc ctgtacttag   18360 tatgggctt  tttcatatgg agagccataa tggagaagta cacattaaca aaacttcccg    18420
attcagttac acatgttttt attgactctg acagtattgc ctataaaggt gcttgtgtag   18480
ttgagaaagc aaaatataaa tatgtcaata aactcacagc agaagaatct gagccatttg   18540
ataatgcgaa agatgctgca agatggttag cagaccagag aatccttgtg gaagagcttg   18600
gcctaacatt tgatgaagat gaatgggaaa gacagacttg gaaagaagct aagagtgaaa   18660
aagaagctat catggctact cagcaggttc ttcaggaatg gcttaaggtt gttggtaaag   18720
aaagaacttg ggtaggttac ttaacagaga aggtgtaca  taaacataaa gacgttaaag   18780
gtcttgagca ccaatatcaa ggtaaccgta agatgctgt  cacaccaaca cacttagttg   18840
cttgtcgtga gtatcttctg tcaagaccag agtttaaatt gattcttgat ggatttgaag   18900
ctgactctat cgttatcgct aaagctgaaa agatgggaaa aaaggctgcc ttaatgagta   18960
ttgataaaga ccttcgccaa gctgaaggta cttactgcat tgatatgacc tatgaaaaat   19020 caccttttaat tttcattgct gataacaacg ttggtgaaat ttgggattgt ccaataaaat   19080
cgacaccaaa agctaagaag acagttggtg taggttttaa atttctttgt tatcaagctg   19140
tggctggtga taatgcggat aattactttg gtttaaaggg tgttggcaaa gctgctgtga   19200
tgaaggctct tgaagggaaa acaacttaca aagagtgtct tgatgcaatt tacgaactat   19260
atgctaagaa agactcctac acttatgtat catgggatgg tcaaacaatt accagaacac   19320
ctttagaatt aatgcagcaa cactttttct tagcttatca ggaaagaaat aaaaaagacg   19380
attttacttt tgataagtat gggtggacac caaatgttaa ctcaacaaac tcttaaaagag  19440 tacctgcact atgaccccga acagggggtc tttacttgga ttaagaagtc tgctaagcac   19500
acaaaaattg gttctgttgc aggtacaaac ttaaggggat acatcagaat ctatttgttt   19560
ggtaagggtt attatgcaca tacactggct gtcctgtata tggatggtta ccttcctgag   19620
tgtgttgacc ataaaaacca tgtaacccta gataatcgct ggataaatct tagggcatgt   19680
acgttatcag agaaccaatg taataggtta ctcaataaga ataataaatc aggtgttaaa   19740
ggtgtgtact acaaaaaaca gtatggtaag tggtctacac agataacttt taagaagaga   19800
gtttacttct tcggcaacta tgacacgatt gctgaagcag cagaggttgt aaatagggaa   19860
cgccaacgtt tacacaaaga gtttgctaat aaaggtgatg aatgagaaaa ataaaaggtt   19920
ttggcaattg ccctgaatat ggacattgga tttcactatg tggtgaagtt gacccagcaa   19980
agcactttgg ttttgtctac ctagtgtact gcaaaaagac tggacagtat tatttgggta   20040
agaaacagct taatagtgtg accaaaagaa aagttgctgg caagactcgg aagaaggtag   20100
tcactaagga gagtgattgg atgacttatg agacttcttc tgagtatatt aaaaaagata   20160
ttgagagctt tggaaaagaa ttttttgact tttacattat ccaaacctac tacacgaaag   20220
```

```
gtggtctagt ttatggtgaa gcaaaccttc aacataagtt cgatgtaatg acaaaaagga    20280
ttgactcgaa gctcagactc ttctacaatg ccaatattgc agcaattaag tttatcacta    20340
aagaaactta tgaagacgct gaaaaaagaa tccataaggt aatgaaagca aattgtgctt    20400
gataactatt gagagagagt aaaatgttta acaaaagcaa agctgtgagt catgtagcaa    20460
aagttgacag caagattgaa gaacttgagc gcattcttgc aaatgccaga gagtcaataa    20520
ttaaagaagt tgaagctgtt gaatctcaaa tgcagcacct aatgcttaaa cgtcaagagc    20580
tacgtgagca tctggagtat attgaaacgc gagagctaaa ggttaacaaa tattttaagg    20640
agtccgaatg tttaactcaa gagaatcagt aaaaaactgg aacctgcgtt gtggaaacac    20700
ccaaaagcaa ccttacagtg atgagtattg ggaatctttg aaatcccagt ctctgtgtat    20760
gcttgaagaa gcaaaagagc ttgtaaaagc aattgaagag aaagacccca ttgagacact    20820
ggatgctcag gcagatttgc aatatgttct tgatggtctg atttatctgt cacaacatga    20880
ccataacggt gctatgaaag ctgtttgcca taataatgac ctgaagtaca cagatgacta    20940
tgaagaagc                                                           20949
```

<210> SEQ ID NO 3
<211> LENGTH: 18448
<212> TYPE: DNA
<213> ORGANISM: Artificial Sequence
<220> FEATURE:
<223> OTHER INFORMATION: Novel Bacteriophage CJ26

<400> SEQUENCE: 3

```
tatgttatct cttcagtctc tgtagattta acaaataggg gtgagtaaaa atgagttcga     60
atatcttcag acttgctgat agattattca accaaccttt actagccact gaatcattag    120
ctcactcagc agcaacttat gtgaataaca gattgctggg tgatgtccaa gcagcagtaa    180
actttgataa cccaaaaggt gatgcaagaa gtcttttaaa agtaaaagat gatattgcta    240
ttatccctat tatgggtggt ttaactcatc gtatgacatt cattgatgca atgtgtacag    300
gtggattaag ctcttatgaa ggtttacgca gaggctttga cgaagcttta gcagatgagt    360
caattaagac tattgttctg catattgatt ctggtggtgg tgaagcttca ggttgctttg    420
aattagcacg tcacattatg gcttcaagag gccaaaagaa aattattgct tatgtagatg    480
agttcgcttg ttccgctgca tatgcccttg catcttctgc tgaagaaatt attgcatcac    540
cagatgcaga tgttggttct attggtgtaa tcatggttca tcaggaatta actaaggcat    600
ttgaaaagaa tggtgtaaca attaacgtca tcaaagctgg tgagtttaaa ggtatgggtt    660
caccattcca agcactttca gaagaaagca agaaagact tcaaaagaga attaatgata    720
cctacgcaac ctttacaggt tttgtagctg aatctcgtaa tctctctgaa gaagctgtaa    780
agaatactga ggcgaatgtt tattctgctc aggaagctct tgaacttggt ttaattaact    840
caatcatgtc tcaagatgat ttcttaaatt acttacaagg ttctgaagag ctccctgtaa    900
gtttaaacgt taacaattca ggtgaagaaa tgactgaaca agaaaagcaa gaactagaag    960
ctttgcgtct tcaggttgct caaatgaaag ctaaagaaca ggaagctgct ttgtcagatt    1020
tgactaataa gatttctgct tctgctgaag cttttggatt tgatgcaaaa gaagctgcaa    1080
cgactatttt aggtgctggt cttgataacc ctctgagcgt tctgtttatg aatgctatgg    1140
aaggtgctaa ccagaaactt aatgaaacta tcgcatccca cgcttctgca atggaagaaa    1200
aagaatcaga aatcaccaag ctgaaagaaa ctgctggtgc tgttcttgaa cactccaacg    1260
```

```
ctatggaaga agtgggtaat gacggcgaag ctgatttggt tgaagaagaa aaagaaccag    1320
ctaagaatgc ttccgaagac accgctgaac aacgcaaact ggctctccag aatgctctaa    1380
aatctcttat caaataagga acacaacaat ggcatatcaa ggttttacta agttaggtaa    1440
aagagaacct ctgaatgata tcattctttg gaacaggtt accccaacag gccactctcg     1500
taaagagtac actccacagg aatctacaga atatcgtgta ggtgaagttc tgaaagcaga    1560
tggtactaag gtacaagctg gggaagaaac tcaggctgat tctgtatgta tcgttaactt    1620
ttatgcagac ctgcaactgt cttaccacgg tcagttgaaa gttgttggta tttaccgtga    1680
tgcagaatta aaagacatgc taactcttga atcaagcgtt gatgctgcta aagtcaagaa    1740
agcactggct gctaaaggta ttgatttcgt accaactggc ctgtaataac aataataaga    1800
cattctggag aattttacaa tgttgactaa ttctgaaaaa agcagatttt tccttgctga    1860
cctgactggt gaagtccagt ctatcccaaa tacttatggg tatatttcca acttaggtct    1920
gttccgttca gcaccaatca cccaaactac tttccttatg gacttgactg attgggatgt    1980
tagcttgctt gatgcggtag accgtgatag ccgtaaagca gagactagcg cacctgagcg    2040
tgtccgtcaa atcagcttcc caatgatgta cttcaaagaa gttgaaagca tcactcctga    2100
tgaaattcag ggtgtacgtc agccaggcac tgcaaatgaa ctgactactg aagctgtagt    2160
acgtgctaag aagctgatga agattcgtac caagttcgat attactcgtg agttcctgtt    2220
tatgcaagcc ctgaagggta agttgttgga tgctcgtggt actctatacg ctgacctgta    2280
caagcagttc gacgttgaga agaagactgt ttacttcgac cttgccaacc ctaatgctga    2340
catcgacgct tctatcgaag aactgcgtat gcacatggaa gacgaagcta agactggcac    2400
tgtaatcaac ggcgaagaaa ttcacgtagt tgttgaccgg gtattcttca gcaaactggt    2460
taagcatcct aagattcgtg acgcttatct tgcacagcag actccgctgg cttggcaaca    2520
gattactggt tctctgagaa ctggtggtac tgacggcgtt caggctcata tgaacacctt    2580
ctactacggt ggtgttaagt ttgtccagta caacggtaag ttcaaagaca gcgtggtaa    2640
ggttcacact ctggtgggca ttgatgatgt agcagcaact gttggtgttg gtcatgcctt    2700
ccctaacgta tctatgctgg gtgaagctaa caacatcttc gaagtggcat atggcccatg    2760
tcctaagatg ggttatgcaa atacacttgg tcaggaactg tacgtattcg aatacgaaaa    2820
agaccgtgac gaaggtattg acttcgaagc tcactcttac atgctgccat actgtactcg    2880
tcctcagttg ctggtagatg ttcgcgctga cgctcaaggt ggctaataaa cttaggaggg    2940
ttattaatgt gttatacagg cgacccagcc aataaccctc ttgatagagt aagaatcctc    3000
tgcacagaca ctaataatga tgaaattctt attgagcagt ctgtgctaga gtggttctat    3060
ctagaatctg gaaaggatga aaagaaagca gccatcaaag ctcttaaata tttactcttt    3120
caagtagcca agatgggaga tgagaaggtt ggtggtgttt acttacgtaa ctcttccaga    3180
ttcaaatctc tgaaagctgt ttatgacgac cttgttaaaa gctctgtttc aggactaccc    3240
tatgcaggtg gtattaatca gtgcgacatt gatatgcgtc gtcagaatcc ttgctctgtc    3300
aagaaataca cagaatatgg tgatgctgcc agatacgaag gcagagatta ctgcaaccgt    3360
gttaatggcg tatttattat cgagcgagat gaataatgt taaaagggtt attcaccccg    3420
ctagagcaaa attagtcggg gctatgaaga acttgcaaac ggctaatgct caagttgggt    3480
attttcaaga acaaggtcaa catagctctg gttttcttta tcctgcttta atgtatttac    3540
aagaagttat tgggggttcct tcagcttctg gtaaagtata tcgtaggttg tttgaaatca    3600
ctatgatgct aaacaaacag accttgttag agcagactaa gaagaatcta tataagcaac    3660
```

```
ttagcagtct caacacagac ccttcaaata ccttagaagc atttgcaaag aatgctcaga   3720
aggcaattaa aagaggtttt ggtaattctg ctatcctccc tcctaacgca ccttccacag   3780
tcaagaaaaa aggctttaac gcacctcttg ttgagacagg tgacttaaga gataaccttg   3840
cttataaaat ttctactaag aagggtatta gaaaatgaga ctcttaaaca gacacagctt   3900
tgtagtaaag cgtaaagtct ctgaagacgg ttattataat gatgatggtg attgggtagc   3960
ttcacaagat attgtagagg ttaactgtaa aggtaatatc cagccataca tcaaaggttc   4020
tgtaaagaat ggtacacaga ttgctttacc ggaaggtatc agacttaccg atacaagaat   4080
cctgtatact acatataaac ttagaacttc agatgatgta gagtggaatg agtctgacat   4140
tgttatgatt gatggtcatg agtatgaagt atttatgact atggattggt cacaacaatt   4200
agcccatacg tcccattacg aatatatcat tattagaagg gataaaatga atgcagttag   4260
aaacagcaga acttgaaaaa ggtctagtta gaaccttagt gggtgttatt ggtcacagac   4320
tagctcgtga taagaataat agaccaaacg taattagagc ttacccttct gataactcaa   4380
atgacaaagg tttaaaacct gaccagccat ttattaccgt atactgtcaa gatgctgcaa   4440
caccttatgg ttgggttctt gataagtttg ttgaggatga tgtagtttgc tacagaattg   4500
cttttcagat tccagtatta attacggtga atggtaaagg tgctcacagt attatgcttg   4560
agcttaaaca acgattagag atgagttcag tcagagattt aatccttgaa gaaacaggag   4620
ctacagtact ggacactgga gcaatcccaa atgattacac ttatctcaat acagatttcg   4680
aaaattctgc acctcttgtt gtaactcttg taaaaaactc agtcctgaaa gatgagcgtg   4740
gaagtattat tgagcgtgtc attgttgatg gtgagttagt ttatgaagaa ggacaagagc   4800
caccagaata tactatccat ctagatgtag actccaaagg ggtaaaataa atgtggaatc   4860
caattgttaa tgtagatatt acattgaaca ccgcaggaac tacaagagaa ggttttggtt   4920
tgccactatt cttagcttca acagataact ttgaagaaag agtgcgtggt tacacttcct   4980
taactgaagt tgctgaagat ttcgatgaga agtctgctgc atataaggct gctaaacaac   5040
tttggagtca gactcctaaa gtaactcagc tttatattgg tagacgtgct atgcagtaca   5100
ctgtatcaat tcctgatgct gttactgaaa gtacagacta ctcaattact gtagctgttg   5160
gtggtggaat ctctcaacca ttccagtata cagcgcaaag ttcagacact gctgaagtag   5220
tgttgcaaca gttaaaaaca cagattgaag ctgactcaac aattaaagat aaggtttctg   5280
tgaacgtaac tggtagtggt gcttctgcca caatgattat taccaaagct ggtgataatg   5340
actttgtgaa agtaacaact acagcacaga ctgtatatat tgcaagtaca actgctgata   5400
cagcatcaac tgctctggca gccattgaag cttattctac tgactggtat ttcattgcag   5460
cagaagatag aactcaacag tttgtcttag caatggcttc tgagattcag gctcgtaaga   5520
aaatcttctt tacagccaac tctgatgtaa cagccctgca aggtacagaa ttagccagtg   5580
caaatgatgt tccagcacag cttgctaaga atatgtacac tcgtacagtt tgcttgtggc   5640
atcacgcagc agcagaagac tatccagaga tggcatacat tgcttatggc gctccatatg   5700
atgcagggtc aattgcttgg ggtaacgctc agttgactgg tgtagctgct tctctacagc   5760
cagctaataa gagacctctg acaagtattc agaagtcagc tttagatgct agacactgta   5820
actttattga ccttgatggt ggtgttccag tggttcgtag agggattact tctggtgggg   5880
aatggattga tatcatccgt ggtgttgact ggttagaatc agacctgaaa acttctctga   5940
gagacttgct aattaatcag aagggtggta agattactta tgatgatact ggtattaccc   6000
```

```
gtattcgtca agtcattgaa acctctctac aaagagcagt caacagaaac ttcctgtcat    6060
cttacacagt taatgttcct aaagcctctc aagttgcttt ggcagacaag aaagctcgta    6120
tcctgaaaga cgttaccttc gcaggtatct tagcaggtgc tatcttggat gttgacttga    6180
aaggtacagt ggcttacgaa taatagaggt aaattggaat ggctatgtat cagcaatatt    6240
cccctaaaga cgttgtatgt agctggaacg gcattgctat tgaaggtttt gccccagact    6300
cattcttacg tctacagaga acatcaccac ttattcacc agttgtaggt gcaggtggtc     6360
aagttgctct gacaagaaat gcagacaaga caggtactat tgagattgag ctaatgcaga    6420
cttctctctc taaccagatg ctttctgcaa ttcaagctaa acaagacaat atggaacttg    6480
aagaagatat ctcttctaac ttcgtaatct acgacccatc aggctctgtt ctggcaactg    6540
gtattaatgc ttggttgcag gaactaccgc agattgaact tggtcgtgac cagaactcta    6600
aaacttggat ttttggttgt gagaagctag aatacacttc tacaattcca gcgtcaagtg    6660
tttaatatat cctataaggg ggagacttta aaggtcttc cccttttttg tttcttttaa     6720
agtattaagg aatcacaatg aaaacagaat ctagagtaat taatggtaag aaagtaaata    6780
tcgttctgct tggggcaaga gatggtatta agatgtctat gaagttgggt aaaattgttg    6840
ttccaacatt tgcacagatg ctatcaagtc tgactgataa agataagaaa gaagttccaa    6900
tggttccatt taaagaactt gttgaagctt gttttgacag aattgaagaa attaaccttg    6960
aagaaatggc taacctatta tttcaaggtg caactattga tgacttccca cttaatattg    7020
atacatactt ccaagcaaac tatggtgaat ttattgatta cttagcattt gcgctggagg    7080
caaacttcgg aagttttttc gaagcaagca ttttcaaaag cctaacttct cagtaaacat    7140
gggtaacact ctacagacac cactaactga tgctgctgta gagtcaacct atgaagaagc    7200
agacgagatg aaatttgtgc ttgctattta tggtatggaa gggtgtaaag aaacacttga    7260
ccaactcttt gctatgacat tctctgattt attatcattg agacaatttc ttgaaattca    7320
gaggtcgtat aaagaggaaa ttgcttacaa cgaacttaga agagcaggaa aaatgtaatg    7380
gcacaatata cagttgatag cttcattgtg aacttggtt tcagtgaaaa ggtaattaaa     7440
ggcttgcaga gagttgagaa gatgtctatg caagctgctc aacgtattga gcgaaatatg    7500
aataaagcct ttgatgtgaa acctaataaa agttctcagg aagcacttaa tagaattgta    7560
aaaaatgctc agtctgcttc gggcagaatc aataaagcac tcaacagttc cttgaacctt    7620
gattcacaag gtgttaaatc tcttaagaga cttgaaactc aagcaaaaaa gactgcaaag    7680
ggtattaaca agtccttaaa agatgctatg aaggttgacg gtaaaatcac tattaagaca    7740
ggtagagggg gaggtggaaa gggaaatccc cctgtcggtg gtggcggtgg acccagaggt    7800
ccgagagtag atgttgctca gagacaaatg gaaagaatgt taacaacaa cttctattca     7860 gggttaaccc gtagactgga acaattggt ggtcaaggta accagatggc agcttctttc     7920
agaggaagct tacaaagtat ctataataaa tacaagggta ctggtaaagt tggtgagtat    7980
gagatggaag ttaaaaagct catcgacgta accaaacgtt gggttattgc agaaaatgct    8040
agactaaaat cagttaaaga agcagcttgg ctacaggata gagctaacgc atcactacgt    8100
caattagttg gtggatttgt ttcagcttat gctttactgg agctatctca aaagactatt    8160
gaggcgggtg taaaaagaca gtctgcacaa ttagcctcta cagctatctt tggagcagat    8220
acacagcaag ccagaatgtt tgctgcatca ttcgcacacc agattggtca gaactacaca    8280
gatactatga agcagtactc aaactttgct gctggtgctc aaccaacact tggttttcag    8340
ggtactcaag agttctataa gaatgctgca atgtttgccc gtatcagagg tgctactgat    8400
```

```
gaagatttga aaggtatcat ggttgcattc cagcagatgg catcaaaagg taaggtacag   8460
gctgaagaac ttcgtggaca gttaggtgac cgtttagcag gtgctgtaca gctattcgct   8520
gatgccattg ggaagactcc acaagaactt gataagttga tgcaagacgg taaacttctt   8580
gctcaagatg ttctgccaaa agtatctgaa aaaatggctg aactggtcaa gcaagcaggt   8640
ggtatgaatg ctgtatctaa gcagaccgct acatcaatgg gccaagctaa ggctatgtgg   8700
gataacacac tcgtagcact gtttaacggc tctagtgagg gtatttcaca gttatctaac   8760
tccgttgcaa tgttcttgca aggttctatg gggactacag aagctttagg tcttgtgatt   8820
gggaatcttt taaaaggtgc tggtaaccta cttgacttcg ttacagactt catgtacaga   8880
gtctctgcac tatactacta tgcaagagct tggtataaag accttgatga cagtcagcaa   8940
aagctagtca aaagtgctgg tgaatttctt ggaacagtca ctatgattgg tgctgctgta   9000
gcaacggttg ctaaagtggc aaagcttatc actggattct ttgatacagc aattgtgaga   9060
aaaatccttc agaggcttgg tattgaagtt gcagaaaaag cagcaccacg agctgcacca   9120
ttgcttgcat ctccagttgg tgttgcagca gcaacgcttg cactatctag gtcttctgac   9180
cctaatgctg gaaagagatt caatgaagct aatatcacta atccttttcaa tgaagctgtt  9240 gcaaatatta caaacccaaa aagaccaatg ttctttgatg agaatgggaa acttaagttt   9300
gcacagtaca ctcaagacat tgagggtaat agaaagctaa ttgacaatgg cctatctaat   9360
tgggatattc tcatggagaa gttatcagca tctcttgata attttgccaa taagtttaat   9420
cagacaccaa tgatgatgac accttctggt ttacctatgc agactaaaca aaccctgaat   9480
gttactttca aacttgatgg taaacaaatt gctactaaga tggtggatat tactgacaag   9540
aatcaagaag acattcttct aagttcaagc tatccagagg aagaataatg ttatgggatt   9600
ctaatatgca aatcaaatat agtggcaaag atggcatcta tttccactta agagataatg   9660
tagatgcctt cttaacctta tcagcaactg aaaacatgga gtttgatagc cctatgcagg   9720
taactacaca gaacatgcaa tcagggcaaa ctgtcacaga taatgtgcaa agagcaccca   9780
gaacaatcac tattagcggt gtcgttgtag ttggctatga agggagctta ttattaactc   9840
gtcagggtca attagtagaa aacttcatcg aaacccttga aaactggcgt gaccagaagc   9900
agattatttc tgtcatctgt aaagatggga ttaaaattga tgattccatt attacgagct   9960
ttaaagcctc taaagatgtt ggtatttcaa acggcctgag aatccagcta acttttcagg  10020
aaattaactt taaagcgatt gtaggacaaa ctgatatttc agcagctact ggcaaaactg  10080
ctaccacgaa tgacggtggt actactagta aaaagaatac agggaacact acaacgagtt  10140
tgggtaatgg caaactaaac tgtcagttgt tattcgacct aaacgccaat ggtgtaaggg  10200
agcttactag tgatgaagac aaggctcttg gaaaatgttc aatgtctgca aagacaagga  10260
agggtgtgac cacattcagt gaagaggctg aaagaaatgc taggtcaaca ttaaacagaa  10320
ctgctggaac tggaaatgcg ttacaaaagc actcagtgaa tccgaataag aaggagactt  10380
attaatgtca caatatattc ctattcctga tacagaatgg tctacacaaa ctgtaaccct  10440
tgatggcact gtctttgtaa ttgagttaaa gtataaagaa aggcttgaca gatggttctt  10500
gacgctatct gatgttgatg gtaatgtatt attacatgaa aagaaatgcc ttgcagacca  10560
atcaatcaca ggacgctatg taattccttc attagctgga gagcttttg ttgaacgaat   10620 gtacggtact ggtttacaac ctaccagaaa taacttcgga agagaaaagg catttgagct  10680
taattattac actcaagaag atatgagatt aatggagaac ttataatgtc tgtaaaagat  10740
```

```
agcactgctg gggcttctttt taggtgctat caattggctg taggtagtga aactacagcc    10800
tttaatgata aacctacaag ccatgctaaa gattctatgc aaatggacta tttcgacaac    10860
ttacaattca cttgtaacgt gtcttatacg tctcagaaga ataaagtaac ctctgatgat    10920
accacttttg aaatctacaa ccttaataaa gagatgagag ccaaattcaa aaccgttggt    10980
gcaacagtta tgctcagagc gggttacact actggtttta aagggacgc aaatggtgac     11040
cttattattg agtatgataa cctcccatta atctatctag gtactattga gtatgcttat    11100
acgtataagc gtggtgtaga tatgattaca aaggttatct gctctaatga taaaatggaa    11160
agaaccacga ttaagacatc aatttcttat aaagcaggaa caacacgtaa aagtgttatt    11220
aaagatttag tcataggct aggcttctcg cttattgatg aagacctttc aagtattgat      11280
ggttatactt ataagaatgg ttttagtgtt tgggggagtg ttgcagaggc actaacaaag    11340
gtctgtgaag agagtagcct gcgttggtat acatttaata agcaaattcg agtagtccct    11400
tttaatgcta aagctagaca gctttcttgg gagatttatc catataacgt tattgactct    11460
ttgcaaggtt actacagaag aactagaaag gttcttaaga aagagaataa gacagttatt    11520
aaagttaaaa ctggagttcg ttgcaaaatc catttagatg gaagaattaa gatgggtgat    11580
aacgtcacta ttagagaaag tgaagatttt gaaggtcagt atcgagtaaa aggtctttct    11640
cataatcttg actttactgg tggctcttgg acaactgaac tagatttaga gaaggtggaa    11700
taatgaagtc accagttact aggatgtcag ggtatgtatc agaatgcctt gatgaattta    11760
gaaaagagat gtatactgga ttaccagcta ttatccagtc ttttgattca aagactcaaa    11820
cagccactgt taagccactt tactcgatta atggttacc tatgccagag attactggtg     11880
tccctgttca atttccaagt ggtggcggag catctttaac atttcccgta aaaactaatg    11940
acagatgctg gttagctttc tcaatgttac ctttagatga cttcgttgtc aatgacaaga    12000
atactcagat ggaaacaaac atgagaagaa cacacgacat ttcagactgt gtagctttcg    12060
taggcatctg tacaagaaca cagaatttta aaccagaccc aacagcagtt agactacatt    12120
tcggtgactc cgtgttaaga gttacagatg atggtaactt ctactttgaa ggtgatgtgc    12180
acatctctaa aaacttatat gtaacagaag aagtgcatgg ttcagatttt atcagtgata    12240
caactggtgt aagctttaat gaacacacgc accattatta ctggacagac cctgctggtg    12300
aggctgatac tacagaggca caataatgaa aacagacttc gcattaaatc taggtggtga    12360
ctatgttgcc acttaggtt cagattcagt gtatgtggct catggtgatt taaagattac     12420
tggtaaccaa attagaatta tcccagaaga tgataaagct actcaggttg ctcaaagact    12480
tcatatcaga tgccttttaa gagctggtga agtcttcttt aatacatctg ctgggttccc    12540
atatttacaa cttgccaaat ttaaacagag aacttctatc tttgataatt acatgaaagc    12600
ataccttgtt gaaacaagag atgtatctaa catctataac tattcttctt caatggataa    12660
tgctcagaga aaagtaactg ttaattttga tgcaactact acaacagata ttttaacaga    12720
cattacgcaa gaggttaata tctaatggca ggattaacta caacaggatt acaaactcta    12780
agatatcagg aaattttga taatatcaaa tcaagacttc ttagagatat ttcaccaaac    12840
cttgacgttt ccgaggatag ccagctaggt ctctttctag cttcaattgc aaggtcttta    12900
gcagacaccc atgaaattct gtcagaaatc tatgatggtg aacgattga caaagctgaa    12960
ggttttaatc tcgatgatat tacagcttta aacgctgtat ataggtatgt ggctcaggct    13020
acaagagggcc aagtagagtt tactggaaca actggtgcaa caattccgtc tacaaccaga    13080
ttaagaagca ctgctggtaa tatcttctat ccagtttcaa acattacatt aacgccttca    13140
```

```
tattgtgttg aagctattct tgaagttaac tctttacgaa ctgatgcaaa ctatgttatt   13200
attattgata acgttatttt ctcttatcag ccaaaacctt cagattcaat cacagtacta   13260
ttaactgagc ttgctaatgc aatcaacggc ggtatcgtag cgaaagcaga agttgtcaat   13320
gatggttcag cattaagggt ttataaagat gaaggtgaca ttattgcaag aaccaaccct   13380
atggttgtaa ctgctacaac gttccttaca ttcacaaaaa ttacaacaat ccacgacgtt   13440
gttgctgagg aatttggtgc aatccctgca ttagctggaa cacttatcga gattgaaaca   13500
actgtagatg gtcttgacag tgtatacaac cgctatgacc tgacaacagg tagaaacgaa   13560
gaaactgata cagaacttcg tcagagatat ttagaatccc tgtcagttac tggtgtagga   13620
actcttgatg caatcgtagc tgctgttaag agggttcagg gtgtatcaga tgcttcaggt   13680
gttgaaaatg atactgaaga acaagctca gaaggacttc caccaaaatc tttcaagatt   13740
gttgtagttg gtggtcaaaa tgataatgtt gctcaagcaa tctgggacac taaacccgct   13800
ggtattaaag cttatggagc tatctttggt acagcttacg acttgggtgg attagctcat   13860
aatatctatt tcagcagacc aacaccaaaa tatgcttttg ttaaagtatc ttactcttta   13920
tatgatgaag aaagcctaac aatcccagaa gaagacatca gagacagtat tgttcaaggt   13980
attaacgctt acggtagaac tttgaaagtt ggtagtgatg ttatccctaa cagaatctac   14040
ggatatattt atgatgtcat caaaggtatt gagattaatg aaatcaaggt agcactttca   14100
aataaccagt cagtacctcc taatgatgga cagtatacta cagcaagaat tactgttgat   14160
ggtgaccaat atactgtatg ggaaagtagc cagtacacca ttgctaagga gtaataatgt   14220
ttcagaaaat tgatgatgtc tactataaga ctcttgacga aagaactgta acacagttta   14280
aagataagtt catctataca agtttactga aagctattac tgatgagttg cagacattgg   14340
aagatgtttc atggcagatg cacactgaaa ggaatattag gaaggcaatt gggcagcaac   14400
ttgataatat tggcacttta atcaaagtcc ccagaccact tggtgctgac gatgaaacat   14460
ataggtcaat gttgtatatc cagattttct taagacgttc tgatacgact ccaacattct   14520
tacagaatgc tattatgaca ctgtataatg caacattttc acaggttttt gaacatatta   14580
cacctatgac tgctggtatt gtaatcaggg ttaacacgag aaacaatgtt cttgatgcag   14640
catacacatt agcaaaaatt tctgccacaa ctattggttc agcggttatt ttaagggatg   14700
ttactttaaa tggtactgct tggacacctg tagaggttgc tgactctgct ttagcaattg   14760
ttgatgacaa agataactgg ttcgttacag atactaacaa aggtcttgtt actaacaata   14820
cagggggttc tttagagaag aacttgctag gaagcttagc agatgctggt gtcagagatg   14880
cttatttcaa ggttgacaga acagctaata gtggctcagt agattactta aaagttaata   14940
aaaattataa cgctacagac aactacatcg ttggtaaaga gactgtagca ggtggtgatt   15000
atggtgttat ggctgaagta gctcaaatca tcaaaggtag aaaagataaa tcacagcaag   15060
aaggaagttc ttaatggcat ttttaaattg gtctacagat gaagtagatg ctgatgtaa   15120 ccagctaaaa gtattaccac caccagaaat tcaggcaact ggcttattaa ggggtgaacc   15180
tatgggtcgc caatggttta attatatctt aaactacctc cttaagaaag caatggtac   15240 tgttggtgaa gtaaggtctt tgccactga gcaaccagat ttagtagcta atggctggag   15300
tcttattaag accgaaacag gtactgcatc aacaagtaca agaaaccttt atacttatga   15360
atttgtagga gctaataat ggcagtaggt gaaattcaaa ttagtgcctt gcctcaagca   15420
gccttaccaa ttgaccttag tgatatcttc catcttaagc agggtattga ggataagaga   15480
```

```
tgcactcttg agcaactact tgctccacac tcaagcctaa gaaacaaccc tcatggtgtt    15540
actaagacac agattggttt agataatgtt attaatgctc ttcagttagt ggctgcaaat    15600
aacttatcag atattactaa tgttgatgag gcaagagcaa atctacagat tatgtcttca    15660
gaagaggtta atagccttgt tcaacagcat attaatgata agagtaaccc acataacaca    15720
actaaggcac aggttggttt aagtaatgtt cagaactgga caacatctaa cctttataat    15780
gaagatgcag ataaatatgc tacagcaaga gcagtaaata acttgtacaa ggctgttcag    15840
gcttcttacc ctgtaggtac attacatctc tcgatgaact ctgctaaccc agctacctac    15900
ctaatttgtg gaggtacttg ggagttggta tcaaaaggac gagcattagt aggttacagt    15960
gacaattcaa gaccagtagg cagtaacttt ggctctagta gtgttagttt gtctagcaac    16020
aatttgccat cacacagtca ttctatctac ctaactggtg gtggtcatac acatggtgct    16080
tccattgcta ttgatagttt tgattatggt actaagggta caagcagttt cgattatgga    16140
acaaaaaaca ctaatactac agggaatcac tcacactcag tcagtggttc taccaatatc    16200
actggtaacc accagcatag tgtaggtggt cgttacggtg tgactctat cggtggtaaa    16260 caacgtgttc aggtctcagg gactgaacag gtttccagtg tagctggcga ccactctcac    16320
actattagtg gctcaactaa tacagttggt aaccactacc atagtgttgc aatcggtgct    16380
cacagccata cagttgggat tggtgctcat acacataaag gtacagtaac tttgcagtca    16440
tctgaacata ctcactcagg tactacaggt gatactggtg ctggtcaagc atttagtgtt    16500
gaacaaccat cctttgtggt ttatgtatgg caaagaaccg cttaaaattc tttacagagg    16560
gttgtatagc cctctttta gaggacaaaa ataatggcag attacaagtt gagtgaatta    16620
aactcaattg atacaattcg ttcagatgac cttctgcatg tcagggttaa aaagagacct    16680
gaaatgttag gtgatgaaga ccgtcgaatg acctatcaag acttcttagc gtcttttaac    16740
cttgagagat ttgttcagat tgctggcagc actatgactg gtgacttagg tattgttaag    16800
ttactttacg gtggtaaggc agtctttgac ccaacaggtt cttctgagat taatattggg    16860
gatgttttaa agactttaa aattaacgca atggtcttta aactaactat tgcagatgct    16920
tcaaggtcgg caactgttta tcatactctg aataagccaa gccctaatga gctttgggatg    16980 agaactaatg aagagaatga tgcaagatac tcaagattag ctgcaaataa cacatttacc    17040
tcccagcagg ttatccaagc aaatggtgaa gctattaggg taaaaaactc ctctgagaac    17100
tcaccgttgt atatcagagg tcaggatagt gctgggaata taggtggta tgtaggtaat    17160 aattcgggga atgatgatgt tcttctctac aacagcaaga caggttctca aattgccgtc    17220
actaatgatg tatctaccaa taaaacacta agaattactg gtcaagttca accttctgac    17280
ttttctaact tagatgctag atactttact cagacagttg ctaatcagaa gtttgcacag    17340
ttagctgggg gtaacacttt tacaggtact aatacttta ctaatcttgt tgttacgaag    17400
aacgctaatg ctcttacttt gcagaatact gatgcaagta caccacttta cattctcggt    17460
aagaagtctg atggaacaaa taatggtat gttggtacag attctgaaga tacacgtcta    17520
aacatttata actaccttac aggttcgcag gtttcactag gtacaactat tggtatcaat    17580
aaaaccgtgc aaatcactgg gcaggttcaa ccctcagact tctctaatat tgattctaga    17640
tatattccgg cagcgacgtt aagtacgatt gcaagaacta atgctgctaa cacattctct    17700
gcacaacagg ttatcaactc tgatggtgaa gctctcgtat tacgagcaaa aactacatcg    17760
tcattgtttt ttagagccaa agatactgat ggagcaagta atggtttgt tggtaatgga    17820 gatgccggtg acgcattagg cctgtataac taccggacag gcaagggggct tactattgat    17880
```

```
tcagtattta gaatgaatgc aaatttatca atcactggtc aagttcaacc ttcagatttc   17940
tctaacttag atgctagata cttgaaagtt tctggtagca cagcaactaa tcttgtaatc   18000
acagaaactg gtcatgggtt atcaactggt agaaattttg caattaatac tagggatgct   18060
ttcaataggg tttgtggttg gtctgctatg actagggtat caaatattcc taattaccca   18120
ttgggcccaa acgcatatat gtttgtattt ggtaaaagag acacttctga acccggtcag   18180
gtcgctttac acaccagcta taacagttct ggattatatt tgtctagatg ccaaactcag   18240
tctgatgagg tcatgtttga aaaaatctat acagataaaa caaaaccaac accttcagag   18300
cttggtgcat acactaaagc tgaaactgac cagaagattg cacaggcaat tagtgactct   18360 acagaccttta ataaaatcta tccagtaggt attgtaacgt ggtttaacag taatgttgac   18420
cctaatacag cactacctgg gttaactt                                      18448
```